(12) United States Patent
Rhodes et al.

(10) Patent No.: US 12,178,941 B2
(45) Date of Patent: *Dec. 31, 2024

(54) ADJUSTABLE BONE IMPLANT FOR ENCLOSING BONE MATERIAL

(71) Applicant: Warsaw Orthopedic, Inc., Warsaw, IN (US)

(72) Inventors: Cheyenne S. Rhodes, Cordova, TN (US); Daniel A. Shimko, Germantown, TN (US)

(73) Assignee: Warsaw Orthopedic, Inc., Warsaw, IN (US)

( * ) Notice: Subject to any disclaimer, the term of this patent is extended or adjusted under 35 U.S.C. 154(b) by 407 days.

This patent is subject to a terminal disclaimer.

(21) Appl. No.: 17/006,006

(22) Filed: Aug. 28, 2020

(65) Prior Publication Data

US 2022/0062508 A1 Mar. 3, 2022

(51) Int. Cl.
| A61L 31/00 | (2006.01) |
| A61L 27/10 | (2006.01) |
| A61L 27/22 | (2006.01) |
| A61L 27/36 | (2006.01) |
| A61L 27/58 | (2006.01) |

(52) U.S. Cl.
CPC .............. *A61L 27/58* (2013.01); *A61L 27/10* (2013.01); *A61L 27/227* (2013.01); *A61L 27/3608* (2013.01); *A61L 2430/02* (2013.01)

(58) Field of Classification Search
None
See application file for complete search history.

(56) References Cited

U.S. PATENT DOCUMENTS

| 6,585,755 | B2 | 7/2003 | Jackson et al. |
| 6,719,795 | B1 | 4/2004 | Cornwall et al. |
| 9,050,111 | B1 | 6/2015 | Temple et al. |
| 9,333,082 | B2 | 5/2016 | Wei et al. |
| 9,913,676 | B2 | 3/2018 | Schlachter et al. |
| 10,064,726 | B1 | 9/2018 | Wei |
| 10,368,930 | B2 | 8/2019 | Schlachter et al. |
| 10,442,175 | B2 | 10/2019 | Schlachter |
| 2008/0317817 | A1 | 12/2008 | Fischer |
| 2010/0055149 | A1* | 3/2010 | Li ............. A61F 2/04 156/193 |
| 2015/0245921 | A1 | 9/2015 | Shimko et al. |
| 2018/0263779 | A1 | 9/2018 | Scarborough et al. |
| 2018/0311049 | A1 | 11/2018 | Shimko et al. |
| 2019/0015209 | A1* | 1/2019 | Scifert ............ A61F 2/2846 |
| 2019/0021862 | A1 | 1/2019 | Kalpakci et al. |
| 2019/0274790 | A1 | 9/2019 | Karmon |
| 2019/0336191 | A1 | 11/2019 | Schlachter et al. |

FOREIGN PATENT DOCUMENTS

| WO | 2007143698 A2 | 12/2007 | |
| WO | WO-2009009688 A1 * | 1/2009 | ......... A61B 17/7097 |

OTHER PUBLICATIONS

International Search Report and Written Opinion of the International Searching Authority dated Dec. 2, 2021 issued in corresponding International PCT Application No. PCT/US2021/047805 filed Aug. 26, 2021.

* cited by examiner

*Primary Examiner* — Susan T Tran

(74) *Attorney, Agent, or Firm* — Sorell, Lenna & Schmidt, LLP

(57) ABSTRACT

A bone implant for enclosing bone material is provided. The bone implant comprises a covering, which can be a biodegradable mesh. The covering is configured to be rolled into a diameter to at least partially enclose the bone material within the covering. In some embodiments, the covering also includes a closure member, the closure member configured to hold the covering in a rolled configuration to a predetermined diameter to at least partially enclose the bone material. A kit and a method of using the bone implant are also provided.

17 Claims, 5 Drawing Sheets

ADJUSTABLE BONE IMPLANT FOR ENCLOSING BONE MATERIAL

BACKGROUND

The use of bone grafts and bone substitute materials in orthopedic medicine is known. While bone wounds can regenerate without the formation of scar tissue, fractures and other orthopedic injuries take a long time to heal, during which time the bone is unable to support physiologic loading unaided. Metal pins, screws, rods, plates, and meshes are frequently required to replace the mechanical functions of injured bone. However, metal is significantly stiffer than bone. Use of metal implants may result in decreased bone density around the implant site due to stress shielding. Physiologic stresses and corrosion may cause metal implants to fracture. Unlike bone, which can heal small damage cracks through remodeling to prevent more extensive damage and failure, damaged metal implants can only be replaced or removed. The natural cellular healing and remodeling mechanisms of the body coordinate removal of bone and bone grafts by osteoclast cells and formation of bone by osteoblast cells.

Conventionally, bone tissue regeneration is achieved by filling a bone repair site with a bone graft (e.g., bone material). Over time, the bone graft is incorporated by the host and new bone remodels the bone graft. To place the bone graft, it is common to use a monolithic bone preformed graft or to form an osteoimplant comprising particulated bone in a carrier. Generally, the formed implant, whether monolithic or particulated and in a carrier is substantially solid at the time of implantation and thus does not conform to the implant site. The implant is also substantially complete at the time of implantation and thus provides little ability for customization, for example, by the addition of autograft or alteration of the shape of the implant.

The use of bone grafts is generally limited by the available shape and size of the grafts. Bone grafts often are available preformed and pre-sized. However, many surgeons like to utilize the local bone acquired during surgery by combining it with another graft but cannot do so if that graft is preformed or pre-sized. Patient autograft can be combined with moldable grafts, but these may not be contained and can migrate from the wound site. Further, bone grafts using cortical bone remodel slowly because of their limited porosity. Traditional bone substitute materials are more quickly remodeled but cannot immediately provide mechanical support. In addition, while bone substitute materials can be used to fill oddly shaped bone defects by themselves, such materials are not as well suited for wrapping or resurfacing bone.

Therefore, it would be beneficial to provide bone implants that can be filled with bone material (e.g., natural bone particles and/or synthetic bone particles), can be easily sized in length and diameter or otherwise adjustable at the point of care for implantation at a variety of surgical sites. Bone implants that can be customized in real time to the size and shape of the bone defect in the patient anatomy as well as to the type of bone material to be used would be desirable. Kits and methods relating to filling and implanting these adjustable bone implants would also be desirable.

SUMMARY

Bone implants are provided that can partially or fully enclose bone material and can be easily sealed and implanted at a surgical site. The bone implants can be customized to the size and shape of the bone defect as well as to the type of bone material to be used. Kits and methods relating to filling and implanting these bone implants are also provided.

In one embodiment, a bone implant for enclosing bone material is provided. The bone implant comprises a covering which, in some aspects, is a biodegradable mesh. The covering is configured to be rolled into a diameter to at least partially enclose the bone material within the covering.

In one embodiment, a kit for making a bone implant is provided. The kit comprises the bone implant, which can be a covering. In many aspects, the covering is configured to be rolled into a diameter to at least partially enclose the bone material within the covering. The kit can also include at least one of (i) a plurality of sizing rings or cylinders, the sizing rings or cylinders configured to engage the bone implant to orientate the implant into the desired diameter; or (ii) a funnel having a varied diameter, the funnel configured to load the covering with an amount of the bone material. In some embodiments, the kit can also include a desiccant to prevent hydrolytic degradation during storage.

In one embodiment, a method of implanting a bone implant at a surgical site is provided. The method comprises providing a bone implant comprising a covering, the covering being configured to be rolled into a diameter to at least partially enclose the bone material within the covering; enclosing the bone material in the covering by orientating the covering into a rolled configuration; and placing the bone implant at the surgical site thereby implanting the bone implant at the surgical site.

While multiple embodiments are disclosed, still other embodiments of the present application will become apparent to those skilled in the art from the following detailed description, which is to be read in connection with the accompanying drawings. As will be apparent, the present disclosure is capable of modifications in various obvious aspects, all without departing from the spirit and scope of the present disclosure. Accordingly, the detailed description is to be regarded as illustrative in nature and not restrictive.

BRIEF DESCRIPTION OF THE FIGURES

The present disclosure will become more readily apparent from the specific description accompanied by the following drawings below.

Figure 1:
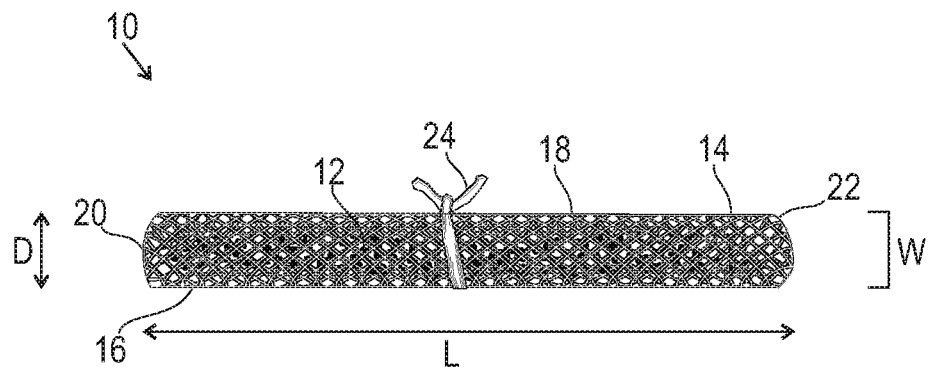
FIG. 1 illustrates a perspective view of a bone implant for enclosing bone material. The bone implant comprises a covering which is a mesh configured to be rolled into a diameter to enclose the bone material within the covering. The bone material is secured within the rolled mesh by a strand used as a closure member tied around the rolled mesh.

It is to be understood that the figures are not drawn to scale. Further, the relation between objects in a figure may not be to scale and may in fact have a reverse relationship as to size. The figures are intended to bring understanding and clarity to the structure of each object shown, and thus, some features may be exaggerated to illustrate a specific feature of a structure.

DETAILED DESCRIPTION

Definitions

For the purposes of this specification and appended claims, unless otherwise indicated, all numbers expressing quantities of ingredients, percentages or proportions of materials, reaction conditions, and other numerical values used in the specification and claims, are to be understood as being modified in all instances by the term "about." Similarly, when values are expressed as approximations, by use of the antecedent "about," it will be understood that the value forms another embodiment that is +/−10% of the recited value. Accordingly, unless indicated to the contrary, the numerical parameters set forth in the following specification and attached claims are approximations that may vary depending upon the desired properties sought to be obtained by the present disclosure. At the very least, and not as an attempt to limit the application of the doctrine of equivalents to the scope of the claims, each numerical parameter should at least be construed in light of the number of reported significant digits and by applying ordinary rounding techniques. Also, as used in the specification and including the appended claims, the singular forms "a," "an," and "the" include the plural, and reference to a particular numerical value includes at least that particular value, unless the context clearly dictates otherwise. Ranges may be expressed herein as from "about" or "approximately" one particular value and/or to "about" or "approximately" another particular value. When such a range is expressed, another embodiment includes from the one particular value and/or to the other particular value.

Notwithstanding that the numerical ranges and parameters setting forth the broad scope of this application are approximations, the numerical values set forth in the specific examples are reported as precisely as possible. Any numerical value, however, inherently contains certain errors necessarily resulting from the standard deviation found in their respective testing measurements. Moreover, all ranges disclosed herein are to be understood to encompass any and all subranges subsumed therein. For example, a range of "1 to 10" includes any and all subranges between (and including) the minimum value of 1 and the maximum value of 10, that is, any and all subranges having a minimum value of equal to or greater than 1 and a maximum value of equal to or less than 10, for example, 5.5 to 10.

Bioactive agent or bioactive compound or bioactive material as used herein is used interchangeably to refer to a compound or entity that alters, inhibits, activates, or otherwise affects biological or chemical events. For example, bioactive agents may include, but are not limited to, osteogenic or chondrogenic proteins or peptides, anti-AIDS substances, anti-cancer substances, antibiotics, immunosuppressants, anti-viral substances, enzyme inhibitors, hormones, neurotoxins, opioids, hypnotics, anti-histamines, lubricants, tranquilizers, anti-convulsants, muscle relaxants and anti-Parkinson substances, anti-spasmodics and muscle contractants including channel blockers, miotics and anticholinergics, anti-glaucoma compounds, anti-parasite and/or anti-protozoal compounds, modulators of cell-extracellular matrix interactions including cell growth inhibitors and antiadhesion molecules, vasodilating agents, inhibitors of DNA, RNA or protein synthesis, anti-hypertensives, analgesics, anti-pyretics, steroidal and non-steroidal anti-inflammatory agents, anti-angiogenic factors, angiogenic factors, anti-secretory factors, anticoagulants and/or antithrombotic agents, local anesthetics, ophthalmics, prostaglandins, antidepressants, anti-psychotic substances, anti-emetics, and imaging agents. In certain embodiments, the bioactive agent is a drug. Bioactive agents further include RNAs, such as siRNA, and osteoclast stimulating factors. In some embodiments, the bioactive agent may be a factor that stops, removes, or reduces the activity of bone growth inhibitors.

In some embodiments, the bioactive agent is a growth factor, cytokine, extracellular matrix molecule or a fragment or derivative thereof, for example, a cell attachment sequence such as RGD. In some embodiments, the bioactive active comprises nutraceuticals, including, but not limited to vitamin A, vitamin D, vitamin E, vitamin K2, isoflavones, milk proteins, caffeine, sugars, or a combination thereof.

Biocompatible, as used herein, is intended to describe materials that, upon administration in vivo, do not induce undesirable long-term effects.

Bone, as used herein, refers to bone that is cortical, cancellous, or cortico-cancellous of autogenous, allogenic, xenogenic, or transgenic origin.

Bone graft, as used herein, refers to any implant prepared in accordance with the embodiments described herein and therefore may include expressions such as bone material and bone membrane.

Bone material includes demineralized bone. Demineralized, as used herein, refers to any material generated by removing mineral material from tissue, for example, bone tissue. In certain embodiments, demineralized bone material may be added to the bone void filler. The demineralized bone material described herein include preparations containing less than 5%, 4%, 3%, 2% or 1% calcium by weight. Partially demineralized bone (for example, preparations with greater than 5% calcium by weight but containing less than 100% of the original starting amount of calcium) is also considered within the scope of the disclosure. In some embodiments, partially demineralized bone contains preparations with greater than 5%, 10%, 15%, 20%, 25%, 30%, 35%, 40%, 45%, 50%, 55%, 60%, 65%, 70%, 75%, 80%, 85%, 90%, 95%, 96%, 97%, 98% or 99% of the original starting amount of calcium. In some embodiments, demineralized bone has less than 95% of its original mineral content. In some embodiments, demineralized bone has less than 95%, 90%, 85%, 80%, 75%, 70%, 65%, 60%, 55%, 50%, 45%, 40%, 35%, 30%, 25%, 20%, 15%, 10%, or 5% of its original mineral content. Demineralized is intended to encompass such expressions as "substantially demineralized," "partially demineralized," "superficially demineralized," and "fully demineralized." In some embodiments, part, or all the surface of the bone can be demineralized. For example, part or all of the surface of the bone material can be demineralized to a depth of from about 100 to about 5000 microns, or about 150 microns to about 1000 microns. In some embodiments, part or all of the surface of the bone material can be demineralized to a depth of from about 100, 150, 200, 250, 300, 350, 400, 450, 500, 550, 600, 650, 700, 750, 800, 850, 900, 950, 1000, 1050, 1100, 1150, 1200, 1250, 1300, 1350, 1400, 1450, 1500, 1550, 1600, 1650, 1700, 1750, 1800, 1850, 1900, 1950, 2000, 2050, 2100, 2150, 2200, 2250, 2300, 2350, 2400, 2450, 2500, 2550, 2600, 2650, 2700, 2750, 2800, 2850, 2900, 2950, 3000, 3050, 3100, 3150, 3200, 3250, 3300, 3350, 3400, 3450, 3500, 3550, 3600, 3650, 3700, 3750, 3800, 3850, 3900, 3950, 4000, 4050, 4100, 4150, 4200, 4250, 4300, 4350, 4400, 4450, 4500, 4550, 4600, 4650, 4700, 4750, 4800, 4850, 4900, 4950 to about 5000 microns. If desired, the bone material can comprise demineralized material.

Partially demineralized bone is intended to refer to preparations with greater than 5% calcium by weight but containing less than 100% of the original starting amount of calcium. In some embodiments, partially demineralized bone comprises 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98 and/or 99% of the original starting amount of calcium.

In some embodiments, the demineralized bone may be surface demineralized from about 1-99%. In some embodiments, the demineralized bone is 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98 and/or 99% surface demineralized. In various embodiments, the demineralized bone may be surface demineralized from about 15-25%. In some embodiments, the demineralized bone is 15, 16, 17, 18, 19, 20, 21, 22, 23, 24 and/or 25% surface demineralized.

Demineralized bone matrix (DBM), as used herein, refers to any material generated by removing mineral material from bone tissue. In some embodiments, the DBM compositions as used herein include preparations containing less than 5% calcium and, in some embodiments, less than 1% calcium by weight. In some embodiments, the DBM compositions include preparations that contain less than 5, 4, 3, 2 and/or 1% calcium by weight. In other embodiments, the DBM compositions comprise partially demineralized bone (for example, preparations with greater than 5% calcium by weight but containing less than 100% of the original starting amount of calcium).

Osteoconductive, as used herein, refers to the ability of a substance to serve as a template or substance along which bone may grow.

Osteogenic, as used herein, refers to materials containing living cells capable of differentiation into bone tissue.

Osteoinductive, as used herein, refers to the quality of being able to recruit cells from the host that have the potential to stimulate new bone formation. Any material that can induce the formation of ectopic bone in the soft tissue of an animal is considered osteoinductive. For example, most osteoinductive materials induce bone formation in athymic rats when assayed according to the method of Edwards et al., "Osteoinduction of Human Demineralized Bone: Characterization in a Rat Model," Clinical Orthopaedics & Rel. Res., 357:219-228, December 1998, incorporated herein by reference.

Superficially demineralized, as used herein, refers to bone-derived elements possessing at least about 90 weight percent of their original inorganic mineral content. In some embodiments, superficially demineralized contains at least about 90, 91, 92, 93, 94, 95, 96, 97, 98 and/or 99 weight percent of their original inorganic material. The expression "fully demineralized" as used herein refers to bone containing less than 8% of its original mineral context. In some embodiments, fully demineralized contains about less than 8, 7, 6, 5, 4, 3, 2 and/or 1% of its original mineral content.

The expression "average length to average thickness ratio" as applied to the DBM fibers of the present application means the ratio of the longest average dimension of the fiber (average length) to its shortest average dimension (average thickness). This is also referred to as the "aspect ratio" of the fiber.

Fibrous, as used herein, refers to bone elements whose average length to average thickness ratio or aspect ratio of the fiber is from about 50:1 to about 1000:1. In some embodiments, average length to average thickness ratio or aspect ratio of the fiber is from about 50:1, 75:1, 100:1, 125:1, 150:1, 175:1, 200:1, 225:1, 250:1, 275:1, 300:1, 325:1, 350:1, 375:1, 400:1, 425:1, 450:1, 475:1, 500:1, 525:1, 550:1, 575:1, 600:1, 625:1, 650:1, 675:1, 700:1, 725:1, 750:1, 775:1, 800:1, 825:1, 850:1, 875:1, 900:1, 925:1, 950:1, 975:1 and/or 1000:1. In overall appearance, the fibrous bone elements can be described as bone fibers, threads, narrow strips, or thin sheets. Often, where thin sheets are produced, their edges tend to curl up toward each other. The fibrous bone elements can be substantially linear in appearance or they can be coiled to resemble springs. In some embodiments, the bone fibers are of irregular shapes including, for example, linear, serpentine, or curved shapes. The bone fibers are demineralized, however some of the original mineral content may be retained when desirable for a particular embodiment. In various embodiments, the bone fibers are mineralized. In some embodiments, the fibers are a combination of demineralized and mineralized.

Non-fibrous, as used herein, refers to elements that have an average width substantially larger than the average thickness of the fibrous bone element or aspect ratio of less than from about 50:1 to about 1000:1. The non-fibrous bone elements are shaped in a substantially regular manner or specific configuration, for example, triangular prism, sphere, cube, cylinder and other regular shapes. By contrast, particles such as chips, shards, or powders possess irregular or random geometries. It should be understood that some variation in dimension will occur in the production of the elements of this application and elements demonstrating such variability in dimension are within the scope of this application and are intended to be understood herein as being within the boundaries established by the expressions "mostly irregular" and "mostly regular."

Rolled covering, as used herein, refers to a covering (e.g., mesh) which has been rolled by revolving or turning along its length or width over until it is in a cylindrical or a substantially cylindrical shape.

The term "at least partially enclosed" refers to a covering that partially encloses the bone material. In some embodiments, the covering will have open ends to partially enclose the bone material. These ends can be sutured, sealed, or otherwise closed.

The bone implants, devices, kits, and methods may be employed to treat spinal disorders such as, for example, degenerative disc disease, disc herniation, osteoporosis, spondylolisthesis, stenosis, scoliosis and other curvature abnormalities, kyphosis, tumor, and fractures. The bone implants, devices, kits, and methods may be employed with other osteal and bone related applications, including those associated with diagnostics and therapeutics. They may also be alternatively employed in a surgical treatment with a patient in a prone or supine position, and/or employ various surgical approaches to the spine, including anterior, posterior, posterior mid-line, direct lateral, postero-lateral, and/or antero-lateral approaches, and in other body regions. The bone implants, devices, kits, and methods may also be alternatively employed with procedures for treating the lumbar, cervical, thoracic, sacral, and pelvic regions of a spinal column. They may also be used on animals, bone models and other non-living substrates, such as, for example, in training, testing and demonstration.

In various embodiments, the bone implant comprises a biodegradable mesh comprising poly(lactide-co-glycolide) (PLGA), polylactide (PLA), polyglycolide (PGA), D-lactide, D,L-lactide, L-lactide, D,L-lactide-co-ε-caprolactone, D,L-lactide-co-glycolide-co-ε-caprolactone, L-lactide-co-ε-caprolactone or a combination thereof.

Bone Implant

Referring to FIGS. 1-3, 4A, 4B, 5A, 5B and 6, a bone implant 10 is provided that is customizable and is configured for enclosing bone material 12. Bone material 12 can be fully or at least partially enclosed by covering 18. The bone implant is configured to be cut and shaped to any size and diameter to match a patient anatomy as required for a particular surgical site. As a result, the customizable covering can be used in a wide array of spinal fusion procedures as well as other applications.

The bone implant is configured, for example, for use in minimally invasive midline lumbar fusion, posterior cervical fusion, and oral maxillofacial repair procedures. The bone implant may also be used in healing vertebral compression fractures, interbody fusion, additional minimally invasive procedures, posterolateral fusion procedures, correction of adult or pediatric scoliosis, treating long bone defects, osteochondral defects, ridge augmentation (dental/craniomaxillofacial, e.g. edentulous patients), beneath trauma plates, tibial plateau defects, filling bone cysts, wound healing, around trauma, contouring (cosmetic/plastic/reconstructive surgery), and others uses.

Covering 18 is biodegradable and is configured to be rolled into a generally tubular conformation having a diameter D for at least partially enclosing bone material 12. It will be understood that the covering can also be made of non-biodegradable or be made of both biodegradable and non-biodegradable material.

Figure 4A:
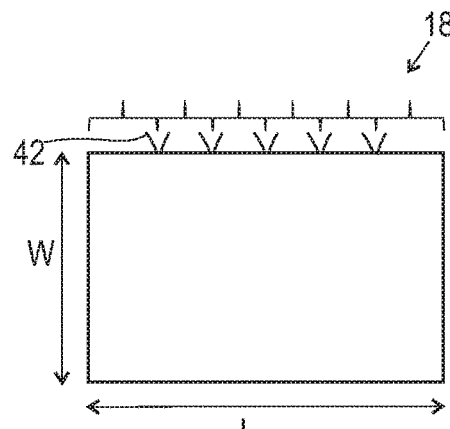
FIG. 4A illustrates a schematic of a flat covering of a bone implant for enclosing bone material. The covering has a certain pre-selected length and width and has a plurality of strands attached at pre-determined intervals on one of its edges. Once the covering is rolled around bone material or graft, the strands can be used to secure the bone material by tying them around the rolled covering. Shown are a plurality of strands at a spaced apart distance from each other disposed on an edge of the covering.
Figure 4B:
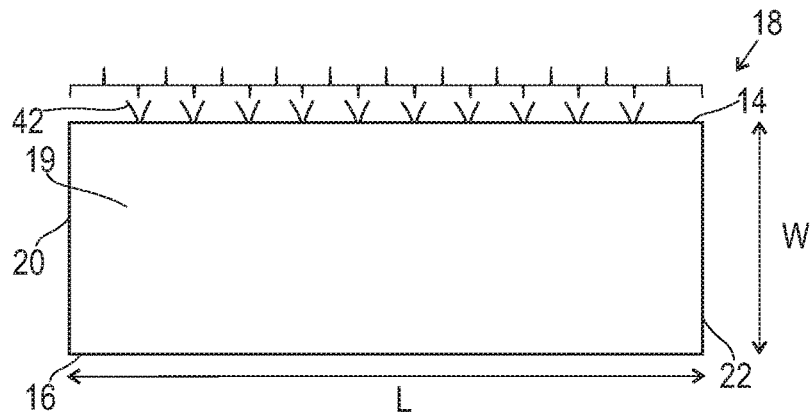
FIG. 4B illustrates a schematic of a flat covering of a bone implant for enclosing bone material, similar to the schematic of FIG. 4A. The covering of this figure has a different pre-selected length and has a plurality of strands attached at pre-determined intervals on one of its edges forming its length. Once the covering is rolled around bone material or graft, the strands can be used to secure the bone material by tying them around the rolled covering.
Figure 6:
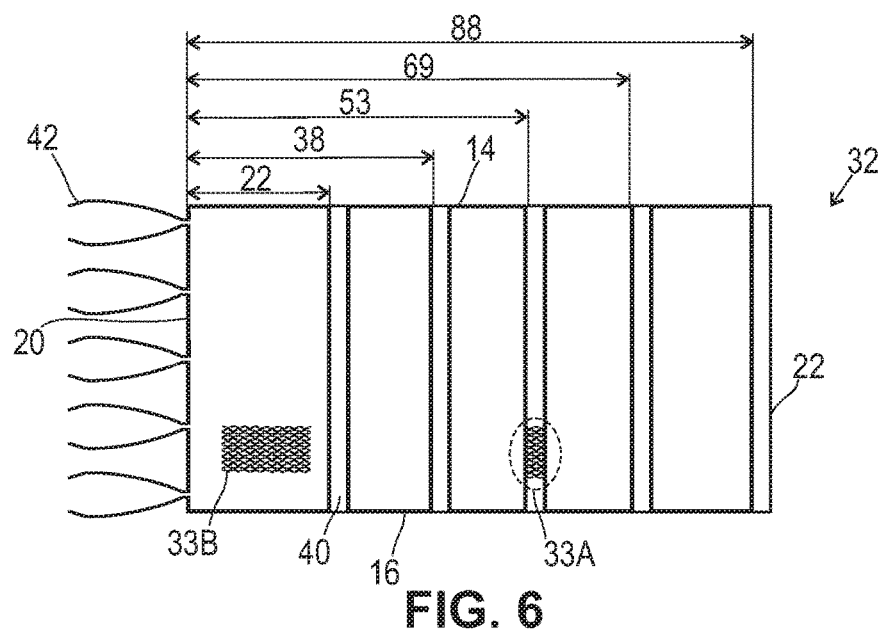
FIG. 6 illustrates a schematic of a flat covering having strands for securing bone material on the width of the covering. The exterior of the covering has visual indicia at pre-defined intervals to help the user to resize the covering to create rolled covering of specific diameters.

Covering 18 defines a generally flat surface 19 which has a first edge 14, a second edge 16, a third edge 20 and a fourth edge 22. First edge 14 is positioned opposite second edge 16 and third edge 20 is positioned opposite fourth edge 22. In some aspects, surface 19 is configured as a square or a rectangle that can be rolled into a different or variable width W, a different or variable length L or a different or variable diameter as illustrated in FIGS. 4A, 4B and 6. In this way, the implant can be customized to meet different sized bone defects.

First edge 14 comprises at least a closure member 24 which is configured to hold coverage 18 in a rolled configuration having a predetermined diameter D for at least partially enclosing bone material 12. In some aspects, third edge 20 and fourth edge 22 can be sealed by suturing or adhesive or other comparable methods by the practicing clinician at the time of use, for example, at a surgical site.

Figure 5A:
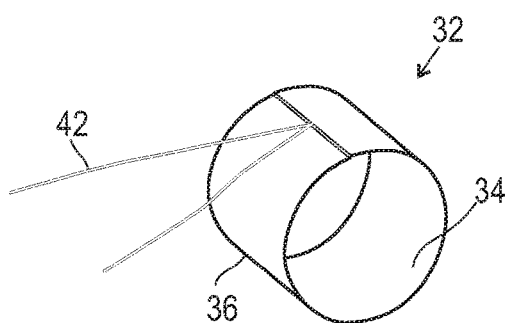
FIG. 5A illustrates a perspective view of a covering in a rolled configuration, shaped as a tube without bone material. The strands around the tube are open.
Figure 5B:
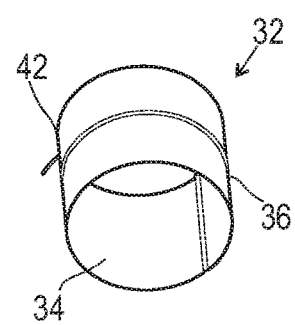
FIG. 5B illustrates a perspective view of the covering of FIG. 5A in a rolled configuration with the strands tied around the rolled covering.

In various embodiments, covering 18 comprises, consists essentially of, or consists of a mesh 32. Mesh 32 has an interior surface 34 and exterior surface 36 as illustrated in FIGS. 5A and 5B. As further described in this disclosure, both the length and width of the mesh can be adjusted by trimming the mesh to any desired size before the mesh is rolled to enclose fully or partially bone material. Thus, the rolled mesh of this application can be customized to match the anatomy of a patient as required at the surgical site.

Either interior surface or exterior surface can comprise a plurality of spaced apart interior indicia 38 (not shown) or exterior indicia 40 configured to aid in sizing of the covering 18 or mesh 32. Indicia 38 can be mesh of different color threads, or other visual indicators, for example, notches, knots, protuberances, and the like. For example, in FIG. 6, indicia 40 comprises different color threads running longitudinally along the length of covering 18 at different lengths to help a surgeon or another clinician to resize the mesh to create a specific diameter of the desired rolled product. Fluorescent surgical dyes and/or color additives approved for use in medical devices can be used. For example, useful dyes include without limitations, D&C Blue No. 6, D&C Blue No. 9, D&C Green No. 5, [phthalocyaninato(2-)]

copper, FD&C Blue No. 2, Chromium-cobalt-aluminum oxide, ferric ammonium citrate, pyrogallol or Logwood extract.

In various embodiments, covering 18 can have different length and width. In some embodiments, the width of covering 18 defines the circumference of the rolled covering and can vary from about 10 mm to about 100 mm, more specifically from about 10 mm, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99 to about 100 mm. In some embodiments, the rolled covering can have a length ranging from about 2 cm, 4, 6, 8, 10, 12, 14, 16, 18, 20, 22, and 24 cm. In one embodiment, the length of the rolled covering can vary from about 4 cm to about 14 cm.

The diameter of the rolled covering can vary from about 2 mm, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99 to about 100 mm. In one embodiment, the diameter of the rolled covering can vary from about 7 mm to about 25 mm.

In the embodiment illustrated in FIG. 6, indicia 40 are disposed at specific lengths along the length of the covering, for example, at 22 mm, 38 mm, 53 mm, 69 mm and 88 mm, which can enable a surgeon to trim the covering at those dimensions.

As illustrated in FIGS. 4A, 4B and 6, at least a closure member 24 can be positioned either on first edge 14 or on third edge 20 of covering 18. In other embodiments, the closure member can be positioned on second edge 16 and/or fourth edge 22. Whether the closure member is attached to the covering or it is separate from it, the closure member role is to hold covering 18 into a rolled configuration for enclosing at least partially bone material 12. As also shown in FIGS. 4A, 4B and 6, closure member 24 can comprise, consist essentially of, or consist of one or more strands 42 configured to be tied. Strands 42 can be disposed at various distances along the length or width of any one of the edges of covering 18.

In some embodiments, the strands are disposed on the edge of covering 18 that is opposite the rolling edge. For example, in one aspect, to roll the covering around second edge 16 would require at least one closure member 24 disposed around first edge 14. In some embodiments, strands 42 can be spaced at pre-defined intervals varying from about 0.5 cm, 0.6, 0.7, 0.8, 0.9, 1.0, 1.2, 1.4, 1.5, 1.6, 1.7, 1.8, 1.9, 2.0, 2.2, 2.3, 2.4, 2.5, 2.6, 2.7, 2.8, 2.9, 3.0, 3.1, 3.2, 3.3, 3.4, 3.5, 3.6, 3.7, 3.8, 3.9, 4.0, 4.1, 4.2, 4.4, 4.5, 4.6, 4.7, 4.8, 4.9, 5.0, 5.1, 5.2, 5.2, 5.3, 5.5, 5.6, 5.7, 5.8, 5.9, 6.0, 6.1, 6.2, 6.3, 6.4, 6.5, 6.6, 6.7, 6.8, 6.9, 7, 7.1, 7.2, 7.3, 7.4, 7.5, 7.6, 7.7, 7.8, 7.9, 8, 8.1, 8.2, 8.3, 8.4, 8.5, 8.6, 8.7, 8.8, 8.9, 9, 9.1, 9.2, 9.3, 9.4, 9.5, 9.6, 9.7, 9.8, 9.9 to about 10 cm. Thus, mesh 32 includes its own self-closure strands 42 which can secure the bone material in the rolled mesh which can be customized to any desired width, length and/or diameter combination. By providing an adjustable mesh with built-in self-closure and/or self-sealing features, the bone material can be fully contained and will not migrate from the surgical site. In this way, mesh 32 enables a clinician to provide a rolled mesh that can be filled with any desired bone material of any type and in any volume.

In FIG. 5A, rolled mesh 32 is illustrated with V-shaped strand 42 in an untied configuration. In FIG. 5B, strand 42 is tied around rolled mesh 32. Similarly, FIG. 1 shows closure member 24 tied around covering 18 with a knot to secure the bone material inside the rolled covering.

The strands can be formed from the same material as the mesh or a different material than the mesh and can be interwoven or integrated in the weave of the mesh. The strands can be manufactured via a coating, 3D printing and/or screen printing. In some embodiments, the strands are made from silk, nylon, cable nylon, polyester, and polypropylene, which are non-absorbable. In other embodiments, the strands are biodegradable and resorbable and can be made from polyglycolic acid (PGA), rapid polyglycolic acid (RPGA), polydioxanone (PDO) and poliglecaprone or polyglycolide co-caprolactone (PGCL).

In various embodiments, the strands can have a length which varies from about 5 cm, 6, 7, 8, 9, 10, 11, 12, 13, 14, 15, 16, 17, 18, 19, 20, 21, 22, 23, 24, 25, 26, 27, 28, 29, 30, 31 to about 32 cm. In many embodiments, the diameter of each strand can vary with their material. For example, in some aspects, for non-absorbable strands, the diameter of each strand can vary from about 0.01 mm, 0.02, 0.03, 0.04, 0.05, 0.06, 0.07, 0.08, 0.09, 0.1, 0.15, 0.2, 0.3, 0.35, 0.4, 0.5, 0.6, 0.7, 0.8 to about 0.9 mm. For resorbable strands, in some aspects, the diameter of each strand can vary from about 0.02, 0.03, 0.04, 0.05, 0.06, 0.07, 0.08, 0.09, 0.1, 0.15, 0.2, 0.3, 0.35, 0.4, 0.5, 0.6, 0.7, 0.8 to about 0.9 mm.

To help the surgeon or clinician resize the cover at the site of surgery, strands 42 are disposed on any one of the edges of covering 18 and can also be of different colors to denote a dimensional length along the cover. Dyes useful for strands of the cover can be the same kind of dyes found useful in coloring other indicia or visual indicators present on covering 18, as illustrated in FIG. 6.

Figure 7A:
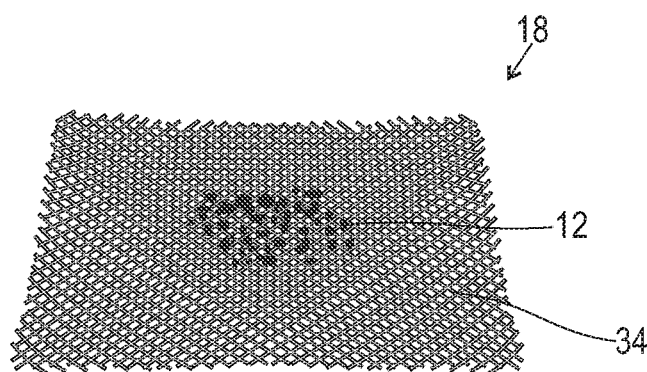
FIG. 7A illustrates a perspective view of a mesh in a flat configuration with bone material on its interior surface.
Figure 7B:
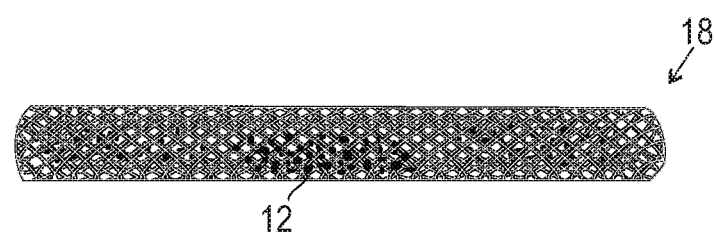
FIG. 7B illustrates a perspective view of the mesh of FIG. 7A in a rolled configuration with bone material enclosed in it.
Figure 7C:
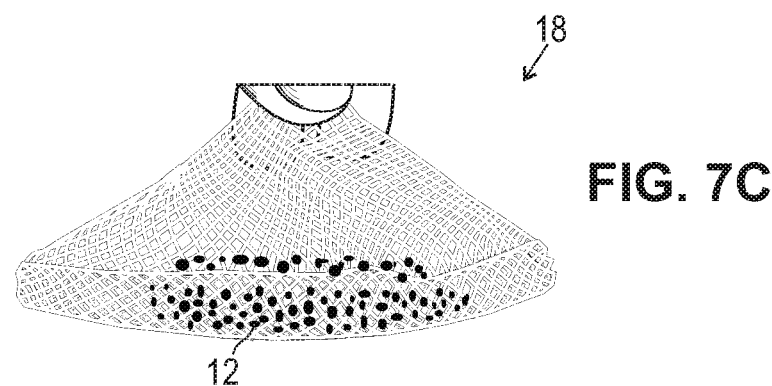
FIG. 7C illustrates a perspective view of the mesh of FIG. 7A in a partially rolled configuration with bone material partially enclosed in the partially rolled mesh.
Figure 7D:
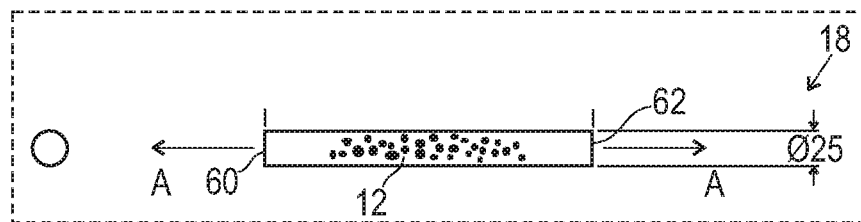
FIG. 7D illustrates a schematic view of the covering (e.g., mesh) rolled into a tubular conformation of a large diameter enclosing bone material. In this embodiment, the diameter of the tube can be reduced by applying pulling forces opposite to each other at the open ends shown by the arrows.
Figure 7E:
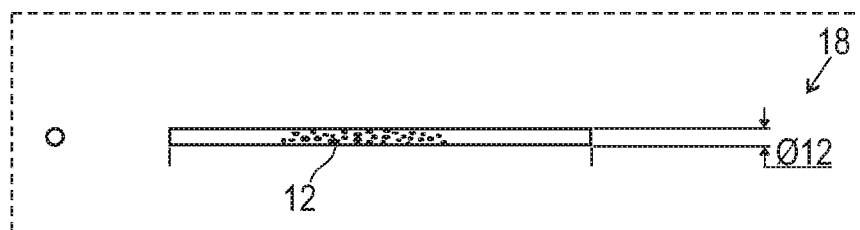
FIG. 7E illustrates a schematic view of the covering rolled into a tubular conformation of a small diameter enclosing bone material. After the diameter of the tube is reduced by applying pulling forces opposite to each other as shown by the arrows in 7D.
Figure 11:
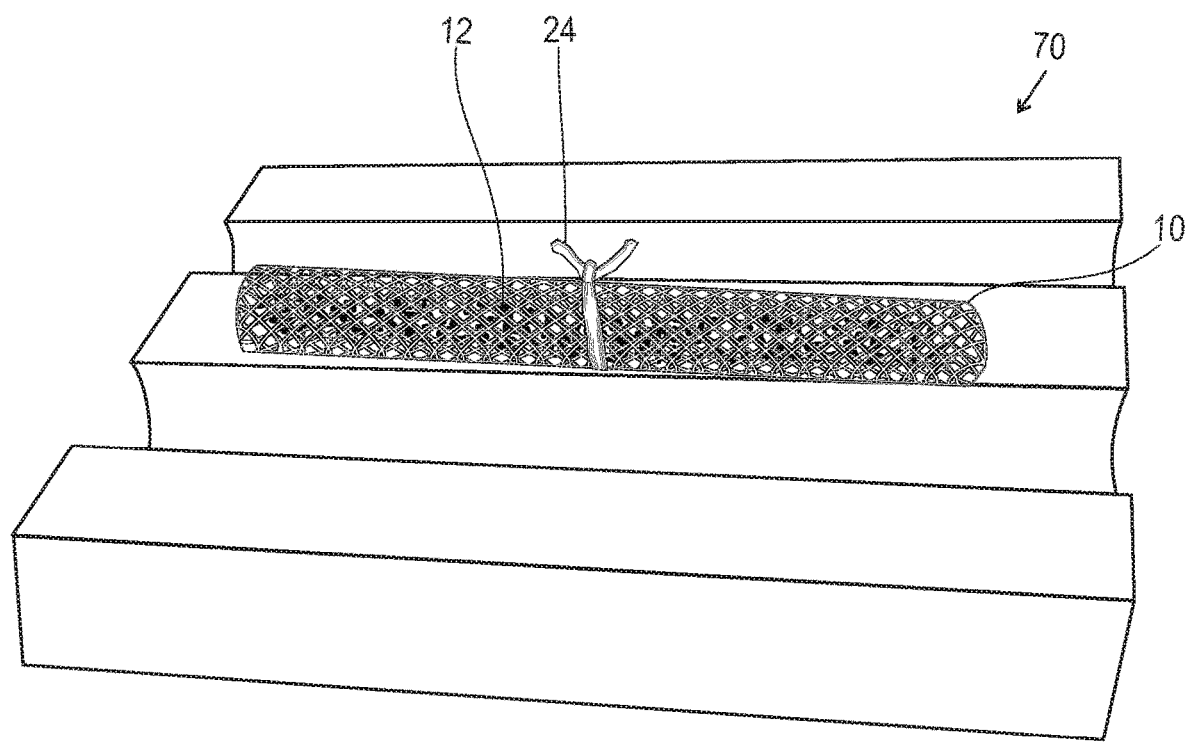
FIG. 11 illustrates a perspective view of a tray including a bone implant enclosing bone material secured by a closing member, which is a strand tied with a knot to hold the covering (e.g., mesh) in a rolled position and enclose the bone material within the covering.

In various embodiments, the covering can have many configurations as illustrated in FIGS. 7A-7E. For example, in FIG. 7A, covering 18 has a planar or unrolled configuration; in FIG. 7B, covering 18 is in a rolled configuration; and in FIG. 7C covering 18 is partially rolled. In FIGS. 7D and 7E, covering 18 has tubular conformations of different diameter sizes where the covering configuration could be described as a porous braided sleeve as illustrated in FIG. 11.

In some embodiments, when in a rolled configuration, covering 18 has opposing open ends 60 and 62, the opposing open ends are configured to be pulled in opposing directions along axis A-A to reduce the diameter of the covering to at least partially enclose the bone material within the covering as illustrated in FIG. 7D. In these embodiments, the clinician will start with a tubular shape with a large diameter, load it with bone graft through end 60 or 62, then pull along the long axis A-A as shown in FIG. 7D, so that the covering can collapse around the enclosed bone material.

Figure 8A:
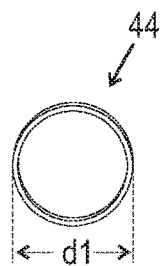
FIGS. 8A, 8B and 8C illustrate sizing rings of different sizes for use in controlling the diameter of a covering as the selected ring is slid over the exterior surface of the rolled covering to allow the covering a uniform diameter and size.
Figure 8B:
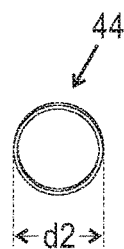
Figure 8C:
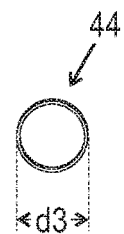
Figure 9A:
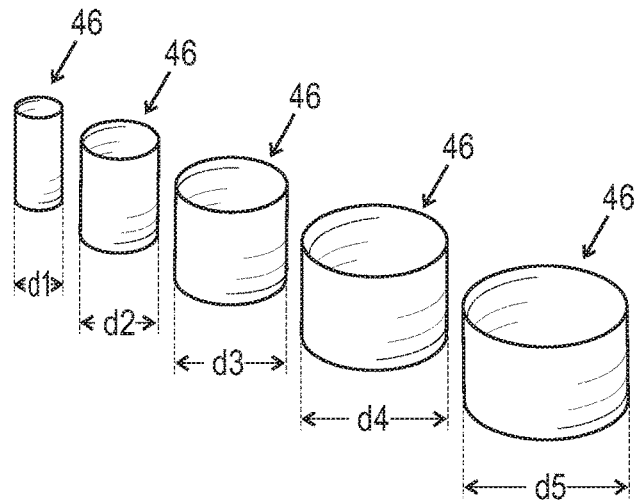
FIG. 9A illustrates a perspective view of sizing cylinders of different sizes that can be used to fill the covering and control the diameter of the covering.

In some embodiments, the tubular covering is configured to be adjusted to varying diameters by using sizing rings 44 of different diameters, for example, d1, d2, d3, etc., as illustrated in FIGS. 8A, 8B and 8C. In other embodiments, as illustrated in FIG. 9A, rather than pulling along the long axis A-A to collapse the rolled covering around the bone material, the clinician can squeeze the bone material inside the tubular covering to a controlled diameter by using sizing cylinders 46 of different diameters. The rings and the sizing cylinders can have diameters that can vary from about 2 mm, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99 to about 100 mm.

Figure 9B:
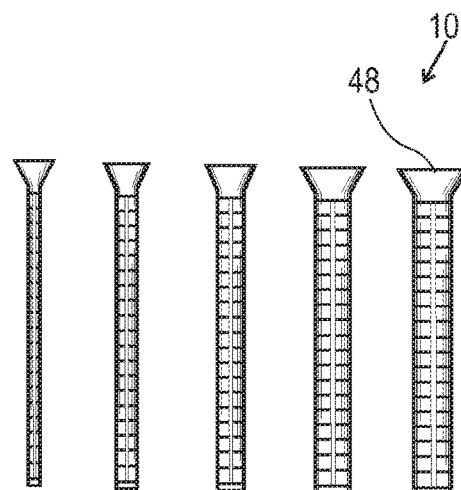
FIG. 9B illustrates rolled coverings of different sizes to be filled with bone material by using funnels of different sizes.
Figure 10:
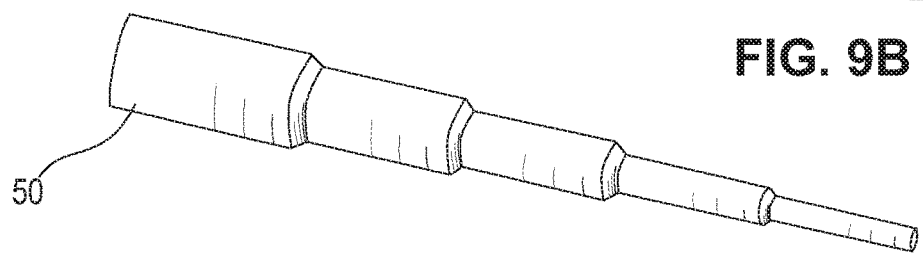
FIG. 10 illustrates a perspective view of a variable diameter funnel that can be used to fill the bone implant (e.g., covering).

In other embodiments, as illustrated in FIG. 9B, the clinician can start with a small diameter covering but enlarge the diameter by adding an excess of bone material. In these embodiments, as illustrated in FIG. 9B, the covering is loaded with bone material using funnels 48 of different diameters. The funnels can have diameters that vary in size from about 2 mm, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99 to about 100 mm. A clinician can reach a similar result by loading the rolled covering with a variable diameter funnel 50 as illustrated in FIG. 10.

Mesh

In various embodiments, covering 18 is an adjustable, biodegradable mesh. The mesh may be made from woven threads that are configured to allow ingrowth of cells while also retaining the bone material within the compartment of the bone implant. The threads of the mesh may have a predetermined thickness of about 0.01 mm to about 2.0 mm, about 0.05 mm to about 1.0 mm, or about 0.1 mm to about 0.5 mm. The thickness of the threads may be uniform along the length of each thread or varied across the length of each thread. In some embodiments, some threads have a greater thickness than other threads. The threads may be sized to allow for customizable pore sizes between the threads. In some embodiments, the bone implant is configured to facilitate transfer of substances and/or materials surrounding the surgical site. Upon implantation to a surgical site, the bone implant may participate in, control, or otherwise adjust, or may allow penetration of the mesh by surrounding materials, such as cells or tissue.

The mesh is configured to be rolled into a diameter as illustrated in FIGS. 1, 2, 3, 5A, and 5B. Alternatively, the mesh could be manufactured in a tubular shape with diameter and length like a braided sleeve 7D and can be resized by applying force A along its length to achieve a new diameter and new length 7E. The mesh is a fully customizable mesh that can be adjusted in both length and diameter to be sized according to the needs of a particular patient anatomy. For example, the mesh may include a diameter dimension between about 1 mm to about 100 mm in diameter. In some embodiments, the mesh includes a diameter of from about 2 mm, 5 mm, 10 mm, 15 mm, 20 mm, 25 mm, 30 mm, 35 mm, 40 mm, 45 mm, 50 mm, 55 mm, 60 mm, 65 mm, 70 mm, 75 mm, 80 mm, 85 mm, 90 mm, 95 mm, or 100 mm. In some embodiments, the mesh includes a length or width between about 0.1 cm to about 24 cm. In some embodiments, the mesh includes a length or width of about 0.1 cm, 0.2, 0.3, 0.35, 0.4, 0.5, 0.6, 0.7, 0.8, 0.9, 1, 2, 3, 4, 5, 6, 7, 8, 9, 10, 11, 12, 13, 14, 15, 16, 17, 18, 19, 20, 21, 22, 23, or 24 cm.

The mesh can be a porous mesh such that fluid transfer and cell infiltration can occur so that osteoblasts can manufacture bone graft. For example, in FIG. 6, mesh 32 illustrates pores at 33A and 33B, which are exploded views. In many embodiments, when the bone material is fully enclosed by the mesh, the mesh is porous to allow influx and efflux of cells. To optimize cell or fluid migration through the mesh, the pore size may be optimized for the viscosity and surface tension of the fluid or the size of the cells. The porous mesh can have a pore size of from about 1 micron to about 2000 microns, from about 1 micron to about 1500 microns, from about 1 micron to about 1000 microns, from about 1 micron to about 500 microns, from about 1 micron to about 250 microns, from about 100 micron to about 2000 microns, from about 150 to about 1500 microns, from about 200 to about 1000 microns, from about 250 to about 500 microns. In some embodiments, the pore size can be about 1, 10, 20, 50, 80, 100, 120, 150, 180, 200, 220, 250, 280, 300, 350, 400, 450, 500, 550, 600, 650, 700, 750, 800, 850, 900, 950, 1000, 1250, 1450, 1650, 1850, 2000, 2100, 2200, 2300, 2400, 2500 or 2600 microns. Generally, the pore size of the mesh should be small enough to retain the bone material from falling through.

The mesh may have varying degrees of permeability across its surface. It may be permeable, semi-permeable, or non-permeable. Permeability may be with respect to cells, to liquids, to proteins, to growth factors, to bone morphogenetic proteins, or other. In further embodiments, the material may be braided.

The mesh may have any suitable custom configuration. In various configuration, the mesh can be customized into a tubular conformation of various diameters and lengths that can easily fit into a patient anatomy.

Additionally, in some embodiments, the flexible character of the rolled mesh allows for the mesh to be manipulated into a plurality of compartments. For example, in a tubular embodiment, the tube may be formed into a plurality of compartments by tying a strand around the tube at one or more points, or by other suitable mechanism such as crimping, twisting, knotting, stapling, or sewing.

In some embodiments, the mesh may be labeled. Such labeling may be done in any suitable manner and at any suitable location on the mesh. In some embodiments, labeling may be done by using a silk screen printing, using an altered weaving, or knotting pattern, by using different colored threads, or other means. The labeling may indicate information regarding the mesh. Such information might include a part number, donor ID number, number, lettering, or wording indicating order of use in the procedure or implant size, etc. In some embodiments, the mesh can be a specific color to help provide the correct orientation of the mesh prior to or during filling and to confirm that the plurality of projections and/or plurality of recesses of the mesh are oriented to optimize their engagement. In some embodiments, a portion of the mesh or the entire mesh is colored blue, purple, pink, orange, yellow, green, or red.

The mesh may be closed after it is rolled to at least partially or fully enclose the bone material. Accordingly, the bone implant may be provided in an unfilled, and unsealed state. After a substance for delivery is placed in the rolled bone implant, the mesh of the bone implant may be permanently or temporarily closed by one or more strands configured to be tied or otherwise secured. Further, temporary closure may be obtained also by fold lock, cinching, adhesive or other means. A temporarily closed bone implant can be opened without damaging the mesh during surgical implantation to add or remove substances in the bone implant.

In some embodiments, the rolled mesh can fully enclose the bone material, where the rolled mesh surrounds the entire bone material (e.g., bone particles, bone cement, etc.) to fully enclose it as illustrated in FIG. 7B. In some embodiments, the mesh can be partially rolled and partially enclose the bone material (e.g., bone particles, bone cement, etc.), where the mesh surrounds a portion of the bone material leaving a portion of the bone material that is not enclosed by the mesh as illustrated in FIG. 7C.

The bone material of the bone implant can comprise fully demineralized bone fibers and surface demineralized bone chips. The bone material may also comprise fibers, powder, chips, triangular prisms, spheres, cubes, cylinders, shards, or other shapes having irregular or random geometries. These can include, for example, "substantially demineralized," "partially demineralized," or "fully demineralized" cortical and/or cancellous bone. These also include surface demineralization, where the surface of the bone construct is substantially demineralized, partially demineralized, or fully demineralized, yet the body of the bone construct is fully mineralized.

In some embodiments, the bone implant is configured to self-seal and to seal and enclose the bone material via chemical fusion, heat treatment, self-fusing materials, self-adhering materials, adhesives, or a combination thereof. In some embodiments, adhesives that can be used include, but are not limited to cyanoacrylates (such as histoacryl, B Braun, which is n-butyl-2 cyanoacrylate; or Dermabond, which is 2-octylcyanoacrylate), epoxy-based compounds, dental resin sealants, dental resin cements, glass ionomer cements, polymethyl methacrylate, gelatin-resorcinol-formaldehyde glues, collagen-based glues, inorganic bonding agents such as zinc phosphate, magnesium phosphate or other phosphate-based cements, zinc carboxylate, L-DOPA (3,4-dihydroxy-L-phenylalanine), proteins, carbohydrates, glycoproteins, mucopolysaccharides, other polysaccharides, hydrogels, protein-based binders such as fibrin glues and mussel-derived adhesive proteins, and any other suitable substance. In some embodiments, the bone implant is sealable via mechanical means such as, for example, zippers, sutures, staples, pins, snaps, clips, or a combination thereof.

In some embodiments, the rolled mesh can remain closed or sealed for from about 1 hour to about 2 hours. The temporary or permanent closure or sealing of the mesh should be compatible and remain functional when used with wet or dry bone material.

In some embodiments, the bone implant is configured to self-seal and to seal and enclose the bone material via chemical fusion, heat treatment, self-fusing materials, self-adhering materials, adhesives, or a combination thereof. In some embodiments, adhesives that can be used include, but are not limited to cyanoacrylates (such as histoacryl, B Braun, which is n-butyl-2 cyanoacrylate; or Dermabond, which is 2-octylcyanoacrylate), epoxy-based compounds, dental resin sealants, dental resin cements, glass ionomer cements, polymethyl methacrylate, gelatin-resorcinol-formaldehyde glues, collagen-based glues, inorganic bonding agents such as zinc phosphate, magnesium phosphate or other phosphate-based cements, zinc carboxylate, L-DOPA (3,4-dihydroxy-L-phenylalanine), proteins, carbohydrates, glycoproteins, mucopolysaccharides, other polysaccharides, hydrogels, protein-based binders such as fibrin glues and mussel-derived adhesive proteins, and any other suitable substance. In some embodiments, the bone implant is sealable via mechanical means such as, for example, zippers, sutures, staples, pins, snaps, clips, or a combination thereof. In some embodiments, the bone implant is sealable by applying a volatile or water-soluble solvent to the mesh material that temporarily softens or causes surface dissolution of the mesh which enables it to bind and adhere to adjacent mesh. Once the volatile or water-soluble solvent is cleared from the application site, the mesh will harden or precipitate creating a bond between the two parts of mesh at the application site of the solvent.

In some embodiments, biological attachment may be via mechanisms that promote tissue ingrowth such as by a porous coating or a hydroxyapatite-tricalcium phosphate (HA/TCP) coating. Generally, hydroxyapatite bonds by biological effects of new tissue formation. Porous ingrowth surfaces, such as titanium alloy materials in a beaded coating or tantalum porous metal or trabecular metal may be used and facilitate attachment at least by encouraging bone to grow through the porous implant surface. These mechanisms may be referred to as biological attachment mechanisms. In some embodiments, the bone implant may be attached to a tissue structure through a wrap, a suture, a wire, a string, an elastic band, a cable or a cable tie, or a combination thereof or another fastener.

In other embodiments, suitable materials that form the mesh of the bone implant include natural materials, synthetic polymeric resorbable materials, synthetic polymeric non-resorbable materials, and other materials. Natural mesh materials include silk, extracellular matrix (such as DBM, collagen, ligament, tendon tissue, or other), silk-elastin, elastin, collagen, and cellulose. Synthetic polymeric resorbable materials include poly(lactic acid) (PLA), poly(glycolic acid) (PGA), poly(lactic acid-glycolic acid) (PLGA), polydioxanone, PVA, polyurethanes, polycarbonates, and others.

In some embodiments, the mesh can be made of a memory shape polymer and/or alloy to allow the mesh to move from a planar configuration to a rolled configuration to enclose at least partially the bone material without the need for a locking or tying mechanism. Memory shape polymers include, but are not limited to polyethers, polyacrylates, polyamides, polysiloxanes, polyurethanes, polyethers amides, polyurethane/ureas, polyether esters, polynorbornene, cross-linked polymers such as cross-linked polyethylene and cross-linked poly(cyclooctene), inorganic-organic hybrid polymers, and copolymers such as urethane/butadiene copolymers, styrene-butadiene copolymers.

The mesh can be absorbable and/or resorbable and be made from a material, including, but not limited to at least one of poly(lactic acid) (PLA), poly(glycolic acid) (PGA), poly(lactic-co-glycolic acid) (PLGA), polydioxanone (PDO), allogeneic collagen, xenogenic collagen, ceramic or a combination thereof. The mesh when formed from an absorbable or resorbable material may be substantially resorbed within 2 weeks, within 4 weeks, within 12 weeks, within 16 weeks, within 20 weeks, within 24 weeks, within 28 weeks, within 32 weeks, within 36 weeks, within 40 weeks, within 44 weeks, within 48 weeks, within 52 weeks or within any other suitable time frame. In some embodiments, the mesh is expected to be resorbed about 6 months after implantation. In various embodiments, the mesh is biocompatible, which means that it is not expected to cause irritation or inflammation of surrounding tissue. To ensure biocompatibility and proper resorption, the pH of surrounding tissue should be greater than about 3. Generally, it is expected that the shelf-life of the mesh useful for the implant described in this disclosure to vary from about 2 to 4 years.

In some embodiments, the mesh itself may be sticky, where, for example, an adhesive agent is applied to the mesh or portions of the mesh so that it can be held in a rolled configuration. The adhesive can be, for example, a bioadhesive, glue, cement, cyanoacrylate, a silicone, a hot melt adhesive and/or cellulosic binder.

The material and configuration of the mesh may be selected or adjusted based on desired release characteristics. Specific properties of the mesh that may be adjusted include thickness, permeability, porosity, strength, flexibility, and/or elasticity. In some embodiments, the thickness and porosity of the mesh may contribute to its strength, flexibility, and elasticity. In some embodiments, the mesh may be made of a squishy, moldable, sticky, and/or tacky material to facilitate placement and packing of the bone implant to a surgical site.

The average molecular weight of the polymer used to make the mesh can be from about 1,000 to about 10,000,000; or about 1,000 to about 1,000,000; or about 5,000 to about 500,000; or about 10,000 to about 100,000; or about 20,000 to 50,000 g/mol. In some embodiments, the molecular weight of the polymer is 1,000, 2,000, 3,000, 4,000, 5,000, 6,000, 7,000, 8,000, 9,000, 10,000, 15,000, 20,000, 25,000, 30,000, 35,000, 40,000, 45,000, 50,000, 55,000, 60,000, 65,000, 70,000, 75,000, 80,000, 85,000, 90,000, 95,000, 100,000, 125,000, 150,000, 175,000, 200,000, 225,000, 250,000, 275,000, 300,000, 325,000, 350,000, 375,000, 400,000, 425,000, 450,000, 475,000, 500,000, 525,000, 550,000, 575,000, 600,000, 625,000, 650,000, 675,000, 700,000, 725,000, 750,000, 775,000, 800,000, 825,000, 850,000, 875,000, 900,000, 925,000, 950,000, 975,000 and/or 1,000,000 Daltons.

The mesh may have varying degrees of permeability. It may be permeable, semi-permeable, or non-permeable. Permeability may be with respect to cells, to liquids, to proteins, to growth factors, to bone morphogenetic proteins, or other substances. The mesh may be 1 to about 30% permeable, from about 30 to about 70% permeable, or from about 70 to about 95% permeable. The mesh may be 1, 5, 10, 15, 20, 25, 30, 35, 40, 45, 50, 55, 60, 65, 70, 75, 80, 85, 90, 95, 96, 97, 98, or 99% permeable.

In various embodiments, the mesh can enclose or partially enclose the bone material (e.g., DBM). In some embodiments, the mesh comprises a polymer matrix that can have in its threads DBM fibers and/or DBM powder, which are suspended in the polymer matrix to facilitate transfer of cells into and out of the mesh bag to induce bone growth at the surgical site. In other embodiments, the mesh further comprises mineralized bone fibers suspended in a polymer matrix. In some embodiments, the DBM powder is suspended in the polymer matrix between the DBM fibers and the mineralized bone fibers. In some embodiments, the DBM powder is suspended between the DBM fibers in the polymer matrix to reduce and/or eliminate gaps that exist between the fibers. In some embodiments, the DBM powder is suspended between the DBM fibers in the polymer matrix to improve osteoinductivity for facilitating bone fusion, for example, interspinous process fusion.

In some embodiments, the polymer matrix comprises a bioerodible, a bioabsorbable, and/or a biodegradable biopolymer that may provide immediate release or sustained release. Examples of suitable sustained release biopolymers include, but are not limited to, poly (alpha-hydroxy acids), poly (lactide-co-glycolide) (PLGA), polylactide (PLA), polyglycolide (PG), polyethylene glycol (PEG), conjugates of poly (alpha-hydroxy acids), polyorthoesters (POE), polyaspirins, polyphosphagenes, collagen, starch, pre-gelatinized starch, hyaluronic acid, chitosans, gelatin, alginates, albumin, fibrin, vitamin E compounds, such as alpha tocopheryl acetate, d-alpha tocopheryl succinate, D,L-lactide, or L-lactide, caprolactone, dextrans, vinylpyrrolidone, polyvinyl alcohol (PVA), PVA-g-PLGA, PEGT-PBT copolymer (polyactive), PEO-PPO-PAA copolymers, PLGA-PEO-PLGA, PEG-PLG, PLA-PLGA, poloxamer 407, PEG-PLGA-PEG triblock copolymers, SAIB (sucrose acetate isobutyrate), or combinations thereof. mPEG and/or PEG may be used as a plasticizer for PLGA, but other polymers/ excipients may be used to achieve the same effect. mPEG imparts malleability to the polymer.

In some embodiments, these biopolymers may also be coated on the mesh to provide a desired release profile or ingrowth of tissue. In some embodiments, the coating thickness may be thin, for example, from about 5, 10, 15, 20, 25, 30, 35, 40, 45 or 50 microns to thicker coatings 60, 65, 70, 75, 80, 85, 90, 95, 100 microns to delay release of the substance from the bone implant. In some embodiments, the range of the coating on the mesh ranges from about 5 microns to about 250 microns or 5 microns to about 200 microns. In some embodiments, the mesh comprises a polymeric coating and the coating comprises a bioactive agent or bioactive material.

Any fully absorbable or resorbable material can be used to fabricate the mesh, such as, for example, absorbable polymers, such as, poly(lactic acid) (PLA), poly(glycolic acid) (PGA), poly(lactic-co-glycolic acid) (PLGA), polydioxanone (PDO), allogeneic collagen, xenogenic collagen, ceramic or a combination thereof. The mesh can be made from thread or yarn that is monofilament or multi filament, and the mesh can be fabricated using knitting, weaving, or it can be non-woven, such as felted or point-bonded, or made with additive manufacturing methods (e.g., 3D printing). U.S. Pat. Nos. 10,064,726 and 10,442,175, incorporated by reference as if set forth in full, describe 3D printing techniques useful for making mesh implants for bone delivery described in this application. The mesh has a pore size that is large enough so that cellular transport and formation of new bone is not impeded. However, the pore size is small enough to adequately contain graft material at an implant site. The bone implant can be various shapes and be provided with instruments designed to ease intraoperative use and assembly. The bone implant enables a streamline assembly. Customization of the bone implant diameter and width enables the bone implant to be used in a variety of bone fusion repair procedures that use a smaller graft size, such as, minimally invasive midline lumbar fusion, posterior cervical fusion and oral maxillofacial repair procedures.

In some embodiments, various components of the mesh comprises poly(lactide-co-glycolide) (PLGA), polylactide (PLA), polyglycolide (PGA), D-lactide, D,L-lactide, L-lactide, D,L-lactide-co-ε-caprolactone, D,L-lactide-co-glycolide-co-ε-caprolactone, L-lactide-co-ε-caprolactone or a combination thereof.

In some embodiments, the mesh further comprises bone morphogenic proteins (BMPs), growth factors, antibiotics, angiogenesis promoting materials, bioactive agents, or other actively releasing materials.

The mesh may be used to deliver a substance comprising any suitable biocompatible material. In specific embodiments, the mesh may be used to deliver surface demineralized bone chips, optionally of a predetermined particle size, fully demineralized bone fibers, optionally pressed, and/or allograft. For embodiments where the substance is a biologic, the substance may be autogenic, allogenic, xenogenic, or transgenic. Other suitable materials that may be positioned in the mesh include, for example, protein, nucleic acid, carbohydrate, lipids, collagen, allograft bone, autograft bone, cartilage stimulating substances, allograft cartilage, TCP, hydroxyapatite, calcium sulfate, polymer, nanofibrous polymers, growth factors, carriers for growth factors, growth factor extracts of tissues, DBM, dentine, bone marrow aspirate, bone marrow aspirate combined with various osteoinductive or osteoconductive carriers, concentrates of lipid derived or marrow derived adult stem cells, umbilical cord derived stem cells, adult or embryonic stem cells combined with various osteoinductive or osteoconductive carriers, transfected cell lines, bone forming cells derived from periosteum, combinations of bone stimulating and cartilage stimulating materials, committed or partially committed cells from the osteogenic or chondrogenic lineage, or combinations of any of the above.

In accordance with some embodiments, the material to be positioned in the hollow area of the rolled mesh may be supplemented, further treated, or chemically modified with one or more bioactive agents or bioactive compounds. Bioactive agent or bioactive compound, as used herein, refers to a compound or entity that alters, inhibits, activates, or otherwise affects biological or chemical events. For example, bioactive agents may include, but are not limited to, osteogenic or chondrogenic proteins or peptides; DBM powder; collagen, insoluble collagen derivatives, etc., and soluble solids and/or liquids dissolved therein; anti-AIDS substances; anti-cancer substances; antimicrobials and/or antibiotics such as erythromycin, bacitracin, neomycin, penicillin, polymyxin B, tetracyclines, biomycin, chloromycetin, and streptomycins, cefazolin, ampicillin, azactam, tobramycin, clindamycin and gentamycin, etc.; immunosuppressants; anti-viral substances such as substances effective against hepatitis; enzyme inhibitors; hormones; neurotoxins; opioids; hypnotics; anti-histamines; lubricants; tranquilizers; anti-convulsants; muscle relaxants and anti-Parkinson substances; anti-spasmodics and muscle contractants including channel blockers; miotics and anti-cholinergics; anti-glaucoma compounds; anti-parasite and/or anti-protozoal compounds; modulators of cell-extracellular matrix interactions including cell growth inhibitors and antiadhesion molecules; vasodilating agents; inhibitors of DNA, RNA, or protein synthesis; anti-hypertensives; analgesics; anti-pyretics; steroidal and non-steroidal anti-inflammatory agents; anti-angiogenic factors; angiogenic factors and polymeric carriers containing such factors; anti-secretory factors; anticoagulants and/or antithrombotic agents; local anesthetics; ophthalmic s; prostaglandins; anti-depressants; anti-psychotic substances; anti-emetics; imaging agents; biocidal/biostatic sugars such as dextran, glucose, etc.; amino acids; peptides; vitamins; inorganic elements; co-factors for protein synthesis; endocrine tissue or tissue fragments; synthesizers; enzymes such as alkaline phosphatase, collagenase, peptidases, oxidases and the like; polymer cell scaffolds with parenchymal cells; collagen lattices; antigenic agents; cytoskeletal agents; cartilage fragments; living cells such as chondrocytes, bone marrow cells, mesenchymal stem cells; natural extracts; genetically engineered living cells or otherwise modified living cells; expanded or cultured cells; DNA delivered by plasmid, viral vectors, or other member; tissue transplants; autogenous tissues such as blood, serum, soft tissue, bone marrow, or the like; bioadhesives; bone morphogenetic proteins (BMPs including BMP-2); osteoinductive factor (IFO); fibronectin (FN); endothelial cell growth factor (ECGF); vascular endothelial growth factor (VEGF); cementum attachment extracts (CAE); ketanserin; human growth hormone (HGH); animal growth hormones; epidermal growth factor (EGF); interleukins, for example, interleukin-1 (IL-1), interleukin-2 (IL-2); human alpha thrombin; transforming growth factor (TGF-beta); insulin-like growth factors (IGF-1, IGF-2); parathyroid hormone (PTH); platelet derived growth factors (PDGF); fibroblast growth factors (FGF, BFGF, etc.); periodontal ligament chemotactic factor (PDLGF); enamel matrix proteins; growth and differentiation factors (GDF); hedgehog family of proteins; protein receptor molecules; small peptides derived from growth factors above; bone promoters; cytokines; somatotropin; bone digesters; antitumor agents; cellular attractants and attachment agents; immuno-suppressants; permeation enhancers, for example, fatty acid esters such as laureate, myristate and stearate monoesters of polyethylene glycol, enamine derivatives, alpha-keto aldehydes; and nucleic acids.

In certain embodiments, the bioactive agent may be a drug. In some embodiments, the bioactive agent may be a growth factor, cytokine, extracellular matrix molecule, or a fragment or derivative thereof, for example, a protein or peptide sequence such as RGD.

The material may have functional characteristics. Alternatively, other materials having functional characteristics may be incorporated into the mesh. Functional characteristics may include radiopacity, bacteriocidity, source for released materials, tackiness, etc. Such characteristics may be imparted substantially throughout the mesh or at certain positions or portions of the mesh.

Suitable radiopaque materials include, for example, ceramics, mineralized bone, ceramics/calcium phosphates/calcium sulfates, metal particles, fibers, and iodinated polymer (see, for example, WO2007/143698). Polymeric materials may be used to form the mesh and be made radiopaque by iodinating them, such as taught for example in U.S. Pat. No. 6,585,755, herein incorporated by reference in its entirety. Other techniques for incorporating a biocompatible metal or metal salt into a polymer to increase radiopacity of the polymer may also be used. Suitable bactericidal materials may include, for example, trace metallic elements. In some embodiments, trace metallic elements may also encourage bone growth.

In some embodiments, the mesh may comprise a material that becomes tacky upon wetting. Such material may be, for example, a protein or gelatin-based material. Tissue adhesives, including mussel adhesive proteins and cryanocrylates, may be used to impart tackiness to the mesh. In further examples, alginate or chitosan material may be used to impart tackiness to the mesh. In further embodiments, an adhesive substance or material may be placed on a portion of the mesh or in a particular region of the mesh to anchor that portion or region of the mesh in place at a surgical site.

Bone Material

The bone material can be natural or synthetic bone material (e.g., tricalcium phosphate and/or hydroxyapatite). In various embodiments, the bone material may be particulated such as, for example, in bone chips, powder or fiber form. If the bone is demineralized, the bone may be made into a particulate before, during or after demineralization. In some embodiments, the bone may be monolithic and may not be a particulate.

The bone may be milled and ground or otherwise processed into particles of an appropriate size before or after demineralization. The particles may be particulate (for example, powder) or fibrous. The terms milling or grinding are not intended to be limited to production of particles of a specific type and may refer to production of particulate or fibrous particles. In certain embodiments, the particle size may be greater than 25 microns, such as ranging from about 25 to about 2000 microns, or from about 25 to about 500 microns or from about 200 to about 1000 microns. In some embodiments, the size of the bone particles are less than 100 microns. In some embodiments, the size of the bone particles are less than 500 microns.

After grinding, the bone particles may be sieved to select those particles of a desired size. In certain embodiments, the particles may be sieved though a 25 micron sieve, a 50 micron sieve, a 75 micron sieve, a 100 micron sieve, a 125 micron sieve, a 150 micron sieve, a 175 micron sieve and/or a 200 micron sieve.

In some embodiments, the bone material comprises DBM and/or mineralized bone. In some embodiments, the size of the bone material is less than 25 microns. In some embodiments, the bone material particle size is about 1, 2, 3, 4, 5, 6, 7, 8, 9, 10, 11, 12, 13, 14, 15, 16, 17, 18, 19, 20, 21, 22, 23, 24 and/or 25 microns.

In various embodiments, the bone powder, chips and/or the DBM and/or mineralized bone fibers have a sticky outer surface such that the bone material can adhere to DBM and/or mineralized bone fibers. In various embodiments, the bone powder is naturally sticky. In some embodiments, an adhesive agent is applied to the bone powder and/or the bone fibers comprising a bio-adhesive, glue, cement, cyanoacrylate, silicones, hot melt adhesives and/or cellulosic binders. In various embodiments, the adhesive may be applied to the surface of the bone powder by spraying or brushing. In some embodiments, a charge is applied to the fibers and an opposite charge is applied to the bone powder, (i.e., the technique of electrostatic precipitation). The bone powder will be attracted to, and tenaciously adhere to, the surface of the fiber. Any of these application techniques can be repeated one or more times to build up a relatively thick layer of adherent bone powder on the surface of the fibers.

The bone powder can be applied directly to the DBM fiber and/or fully mineralized fiber, chips and the mixture can be disposed in the mesh. In some embodiments, the bone material inserted into the mesh contains pores having a pore size from about 0.5 to about 2,000 microns. In some embodiments, bone material inserted into the mesh contains pores having a pore size of from about 0.5, 5, 50, 100, 150, 200, 250, 300, 350, 400, 450, 500, 550, 600, 650, 700, 750, 800, 850, 900, 950, 1,000, 1,050, 1,100, 1,150, 1,200, 1,250, 1,300, 1,350, 1,400, 1,450, 1,500, 1,550, 1,600, 1,650, 1,700, 1,750, 1,800, 1,850, 1,900, 1,950 to about 2,000 microns. In some embodiments, the pore size of the bone material is uniform. In some embodiments, the pore size of bone material is non-uniform and includes various pore sizes in the range from 0.5 to about 2,000 microns. Alternatively, the DBM fibers, chips, and DBM powder can be placed in a polymer (for example, collagen) and inserted into the bone implant.

Following shaving, milling or other technique whereby they are obtained, the bone material is subjected to demineralization in order to reduce its inorganic content to a very low level, in some embodiments, to not more than about 5% by weight of residual calcium and to not more than about 1% by weight of residual calcium. Demineralization of the bone material ordinarily results in its contraction to some extent.

Bone used in the methods described herein may be autograft, allograft, or xenograft. In various embodiments, the bone may be cortical bone, cancellous bone, or corticocancellous bone. While specific discussion is made herein to demineralized bone matrix, bone matrix treated in accordance with the teachings herein may be non-demineralized, demineralized, partially demineralized, or surface demineralized. This discussion applies to demineralized, partially demineralized, and surface demineralized bone matrix. In one embodiment, the demineralized bone is sourced from bovine or human bone. In another embodiment, demineralized bone is sourced from human bone. In one embodiment, the demineralized bone is sourced from the patient's own bone (autogenous bone). In another embodiment, the demineralized bone is sourced from a different animal (including a cadaver) of the same species (allograft bone).

In some embodiments, the bone material can be a combination of patient autograft bone and additional bone materials such as, for example, allograft, allograft DBM, ceramics and/or any of the bone material described above. In some embodiments, the combination bone material can have a ratio of 50:50 autograft bone to additional bone materials. In some embodiments, the combination bone material can have any ratio of autograft bone to additional bones materials, including, but not limited to, 25:75, 75:25, 10:90, 90:10, 20:80, 80:20, 30:70, 70:30, 40:60, or 60:40 autograft bone to additional bone materials.

In some embodiments, the bone material can be from about 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99 to about 100% patient autograft bone, additional bone material or a combination thereof.

Any suitable manner of demineralizing the bone may be used. Demineralization of the bone material can be conducted in accordance with known conventional procedures. For example, in a preferred demineralization procedure, the bone materials useful for the implantable composition of this application are subjected to an acid demineralization step that is followed by a defatting/disinfecting step. The bone material is immersed in acid over time to effect its demineralization. Acids which can be employed in this step include inorganic acids such as hydrochloric acid and organic acids such as peracetic acid, acetic acid, citric acid, or propionic acid. The depth of demineralization into the bone surface can be controlled by adjusting the treatment time, temperature of the demineralizing solution, concentration of the demineralizing solution, agitation intensity during treatment, and other applied forces such as vacuum, centrifuge, pressure, and other factors such as known to those skilled in the art. Thus, in various embodiments, the bone material may be fully demineralized, partially demineralized, or surface demineralized.

After acid treatment, the bone is rinsed with sterile water for injection, buffered with a buffering agent to a final predetermined pH and then finally rinsed with water for injection to remove residual amounts of acid and buffering agent or washed with water to remove residual acid and thereby raise the pH. Following demineralization, the bone material is immersed in solution to affect its defatting. A defatting/disinfectant solution is an aqueous solution of ethanol, the ethanol being a good solvent for lipids and the water being a good hydrophilic carrier to enable the solution to penetrate more deeply into the bone. The aqueous ethanol solution also disinfects the bone by killing vegetative microorganisms and viruses. Ordinarily at least about 10 to 40 weight percent by weight of water (i.e., about 60 to 90 weight percent of defatting agent such as alcohol) should be present in the defatting/disinfecting solution to produce optimal lipid removal and disinfection within the shortest period of time. The concentration range of the defatting solution is from about 60 to 85 weight percent alcohol or about 70 weight percent alcohol.

Further in accordance with this application, the DBM material can be used immediately for preparation of the bone implant or it can be stored under aseptic conditions, advantageously in a critical point dried state prior to such preparation. In one embodiment, the bone material can retain some of its original mineral content such that the composition is rendered capable of being imaged utilizing radiographic techniques.

In various embodiments, this application also provides bone matrix compositions comprising critical point drying (CPD) fibers. DBM includes the collagen matrix of the bone together with acid insoluble proteins including bone morphogenic proteins (BMPs) and other growth factors. It can be formulated for use as granules, pellets, spheres, gels, sponge material or putty and can be freeze-dried for storage. Sterilization procedures used to protect from disease transmission may reduce the activity of beneficial growth factors in the DBM. DBM provides an initial osteoconductive matrix and exhibits a degree of osteoinductive potential, inducing the infiltration and differentiation of osteoprogenitor cells from the surrounding tissues.

DBM preparations have been used for many years in orthopedic medicine to promote the formation of bone. For example, DBM has found use in the repair of fractures, in the fusion of vertebrae, in joint replacement surgery, and in treating bone destruction due to underlying disease such as rheumatoid arthritis. DBM is thought to promote bone formation in vivo by osteoconductive and osteoinductive processes. The osteoinductive effect of implanted DBM compositions is thought to result from the presence of active growth factors present on the isolated collagen-based matrix. These factors include members of the TGF-β, IGF, and BMP protein families. Examples of osteoinductive factors include TGF-β, IGF-1, IGF-2, BMP-2, BMP-7, parathyroid hormone (PTH), and angiogenic factors. Other osteoinductive factors such as osteocalcin and osteopontin are also likely to be present in DBM preparations as well. There are also likely to be other unnamed or undiscovered osteoinductive factors present in DBM.

In various embodiments, the DBM provided in the kits, implants and methods described in this application is prepared from elongated bone fibers which have been subjected to critical point drying (CPD). The elongated CPD bone fibers employed in this application are generally characterized as having relatively high average length to average width ratios, also known as the aspect ratio. In various embodiments, the aspect ratio of the elongated bone fibers is at least from about 50:1 to at least about 1000:1. Such elongated bone fibers can be readily obtained by any one of several methods, for example, by milling or shaving the surface of an entire bone or relatively large section of bone.

In other embodiments, the length of the fibers can be at least about 3.5 cm and average width from about 20 mm to about 1 cm. In various embodiments, the average length of the elongated fibers can be from about 3.5 cm to about 6.0 cm and the average width from about 20 mm to about 1 cm. In other embodiments, the elongated fibers can have an average length from about 4.0 cm to about 6.0 cm and an average width from about 20 mm to about 1 cm.

In yet other embodiments, the diameter or average width of the elongated fibers is, for example, not more than about 1.00 cm, not more than 0.5 cm or not more than about 0.01 cm. In still other embodiments, the diameter or average width of the fibers can be from about 0.01 cm to about 0.4 cm or from about 0.02 cm to about 0.3 cm.

In another embodiment, the aspect ratio of the fibers can be from about 50:1 to about 950:1, from about 50:1 to about 750:1, from about 50:1 to about 500:1, from about 50:1 to about 250:1; or from about 50:1 to about 100:1. Fibers according to this disclosure can have an aspect ratio from about 50:1 to about 1000:1, from about 50:1 to about 950:1, from about 50:1 to about 750:1, from about 50:1 to about 600:1, from about 50:1 to about 350:1, from about 50:1 to about 200:1, from about 50:1 to about 100:1, or from about 50:1 to about 75:1.

In some embodiments, the chips to fibers ratio is about 90:10, 80:20, 75:25, 70:30, 60:40, 50:50, 40:60, 30:70, 25:75, 20:80 and/or 10:90. In various embodiments, a surface demineralized chips to fibers ratio is about 90:10, 80:20, 75:25, 70:30, 60:40, 50:50, 40:60, 30:70, 25:75, 20:80 and/or 10:90. In some embodiments, a surface demineralized chips to fully demineralized fibers ratio is about 90:10, 80:20, 75:25, 70:30, 60:40, 50:50, 40:60, 30:70, 25:75, 20:80 and/or 10:90.

In some embodiments, the DBM fibers have a thickness of about 0.5-4 mm. In various embodiments, the DBM fibers have a thickness of about 0.5, 0.6, 0.7, 0.8, 0.9, 1, 1.5, 2, 2.5, 3, 3.5 and/or 4 mm. In various embodiments, the ratio of DBM fibers to DBM powder is about 40:60 to about 90:10 W/W, W/V or V/V. In some embodiments, the ratio of mineralized bone fibers to DBM powder is about 25:75 to about 75:25 W/W, W/V or V/V. In various embodiments, the bone implant comprises DBM fibers and mineralized fibers in a ratio of 40:60 to about 90:10 W/W, W/V or V/V. In some embodiments, the DBM fibers to DBM powder ratio, mineralized bone fibers to DBM powder ratio and/or the DBM fibers and mineralized fibers ratio is from 5:95 to about 95:5 W/W, W/V or V/V. In some embodiments, the DBM fibers to DBM powder ratio, mineralized bone fibers to DBM powder ratio and/or the DBM fibers and mineralized fibers ratio is 5:95, 10:90, 15:85, 20:80, 25:75, 30:70, 35:65, 40:60, 45:55, 50:50, 55:45, 60:40, 65:35, 70:30, 75:25, 80:20, 85:15, 90:10 and/or 95:5 W/W, W/V or V/V.

In some embodiments, the bone material comprises demineralized bone material comprising demineralized bone, fibers, powder, chips, triangular prisms, spheres, cubes, cylinders, shards, or other shapes having irregular or random geometries. These can include, for example, "substantially demineralized," "partially demineralized," or "fully demineralized" cortical and/or cancellous bone. These also include surface demineralization, where the surface of the bone construct is substantially demineralized, partially demineralized, or fully demineralized, yet the body of the bone construct is fully mineralized.

In various embodiments, the bone material comprises fully DBM fibers and surface demineralized bone chips. In some embodiments, the ratio of fully DBM fibers to surface demineralized bone chips is from 5:95 to about 95:5 fibers to chips. In some embodiments, the ratio of fully DBM fibers to surface demineralized bone chips is 5:95, 10:90, 15:85, 20:80, 25:75, 30:70, 35:65, 40:60, 45:55, 50:50, 55:45, 60:40, 65:35, 70:30, 75:25, 80:20, 85:15, 90:10 and/or 95:5 fibers to chips. In various embodiments, the fully DBM fibers have a thickness of about 0.5-4 mm. In various embodiments, the fully DBM fibers have a thickness of about 0.5, 0.6, 0.7, 0.8, 0.9, 1, 1.5, 2, 2.5, 3, 3.5 and/or 4 mm.

In various embodiments, the fibers and/or the powder is surface DBM. In some embodiments, the fibers and/or the powder is surface DBM cortical allograft. In various embodiments, surface demineralization involves surface demineralization to at least a certain depth. For example, the surface demineralization of the allograft can be from about 0.25 mm, 0.5 mm, 1 mm, 1.5 mm, 2.0 mm, 2.5 mm, 3.0 mm. 3.5 mm, 4 mm, 4.5 mm, to about 5 mm. The edges of the bone fibers and/or powder may further be machined into any shape or to include features such as grooves, protrusions, indentations, etc., to help improve fit and limit any movement or micromotion to help fusion and/or osteoinduction to occur.

DBM typically is dried, for example via lyophilization or solvent drying, to store and maintain the DBM in active condition for implantation. Moreover, each of these processes is thought to reduce the overall surface area structure of bone. As may be appreciated, the structural damage of the exterior surface reduces the overall surface area. Physical alterations to the surface and reduction in surface area can affect cell attachment, mobility, proliferation, and differentiation. The surface's affinity for growth factors and release kinetics of growth factors from the surface may also be altered.

Accordingly, in some embodiments, methods for drying bone to store and maintain the bone in active condition for implantation that maintains or increases the surface area of the bone are provided. In one embodiment, the bone matrix is treated using a critical point drying technique, thereby reducing destruction of the surface of the bone. While specific description is made to critical point drying, it is to be appreciated that, in alternative embodiments, super critical point treatment may be used. In various embodiments utilizing CPD, a percentage of collagen fibrils on the surface of the bone are non-denatured after drying to a residual moisture content of approximately 15% or less. In some embodiments, after drying, the bone matrix has a residual moisture content of approximately 8% or less. In some embodiments, after drying, the bone matrix has a residual moisture content of approximately 6% or less. In some embodiments, after drying, the bone matrix has a residual moisture content of approximately 3% or less.

Evaporative drying and freeze drying of specimens can cause deformation and collapse of surface structures, leading to a decrease in surface area. Without wishing to be bound by a particular theory, this deformation and structure is thought to occur because as a substance crosses the boundary from liquid to gas, the substance volatilizes such that the volume of the liquid decreases. As this happens, surface tension at the solid-liquid interface pulls against any structures to which the liquid is attached. Delicate surface structures tend to be broken apart by this surface tension. Such damage may be caused by the effects of surface tension on the liquid/gas interface. Critical point drying is a technique that avoids effects of surface tension on the liquid/gas interface by substantially preventing a liquid/gas interface from developing. Critical point or supercritical drying does not cross any phase boundary, instead passing through the supercritical region, where the distinction between gas and liquid ceases to apply. As a result, materials dehydrated using critical point drying are not exposed to damaging surface tension forces. When the critical point of the liquid is reached, it is possible to pass from liquid to gas without abrupt change in state. Critical point drying can be used with bone matrices to phase change from liquid to dry gas without the effects of surface tension. Accordingly, bone dehydrated using critical point drying can retain or increase at least some of the surface structure and therefore the surface area.

In some embodiments, critical point drying is carried out using carbon dioxide. However, other mediums such as Freon, including Freon 13 (chlorotrifluoromethane), may be used. Generally, fluids suitable for supercritical drying include carbon dioxide (critical point 304.25 K at 7.39 MPa or 31.1° C. at 1072 psi or 31.2° C. and 73.8 bar) and Freon (about 300 K at 3.5-4 MPa or 25 to 30° C. at 500-600 psi). Nitrous oxide has similar physical behavior to carbon dioxide but is a powerful oxidizer in its supercritical state. Supercritical water is also a powerful oxidizer, partly because its critical point occurs at such a high temperature (374° C.) and pressure (3212 psi/647K and 22.064 MPa).

In some embodiments, the bone may be pretreated to remove water prior to critical point drying. Thus, in accordance with one embodiment, bone matrix is dried using carbon dioxide in (or above) its critical point status. After demineralization, bone matrix samples (in water) may be dehydrated to remove residual water content. Such dehydration may be, for example, through a series of graded ethanol solutions (for example, 20%, 50%, 70%, 80%, 90%, 95%, 100% ethanol in deionized water). In some embodiments, penetrating the tissue with a graded series of ethanol solutions or alcohols may be accomplished in an automated fashion. For example, pressure and vacuum could be used to accelerate penetration into the tissue.

Kits

In some embodiments, a device to hold the mesh while rolling the mesh to at least partially enclose bone material is provided. The device can be a tray and can be positioned in an upright configuration during placement of the bone material into the mesh. The tray can be a thermoform tray comprising a central trough. The tray may or may not be a part of a sterile packaging for the bone implant. The tray may also comprise projections or other features to clip and/or hold the bone implant in a desired spatial arrangement. Suitable trays to fill the covering (e.g., mesh) with bone material are described in Shimko et. al., U.S. Publication No. 20180311049 (U.S. Ser. No. 15/581,817, filed Apr. 28, 2017) and Kalpakci et. al., U.S. Publication No. 20190021862 (U.S. Ser. No. 15/656,112, filed Jul. 21, 2017). The entire disclosure of these applications is incorporated herein by reference.

In various aspects, a kit is provided which comprises bone implant 10 as described herein, including covering 18, which in some aspects can be mesh 32, that is configured to be rolled in a diameter to at least partially enclose bone material 12. The kit can also include at least one of a plurality of sizing rings 44, or a plurality of sizing cylinders 46, or one or more funnels 48 having different diameters, or a funnel having a varied diameter 50. Either the plurality of rings or the plurality of sizing cylinders is configured to engage the bone implant to orientate the implant into the desired diameter. The one or more funnels including the variable diameter funnel are configured to load covering 18 with an amount of bone material. In some embodiments, the kit includes a separate closure member 24, for example a bone suture. In various embodiments, as described above, the closure member can be one or more strands 42 that are attached to mesh 32.

In some embodiments, the mesh can be provided in a rolled configuration and the sizing cylinders 46 can be used to fill the rolled mesh. In this way a predetermined amount of bone material can be added to one or more sizing cylinders to load the desired amount of bone material in the mesh. This can also be accomplished with the variable diameter funnel.

The kit can further comprise bone material, for example, demineralized bone matrix, allograft, xenograft, ceramic of mixtures thereof. In various aspects, the kit can comprise a tray 70 as illustrated in FIG. 11.

In some embodiments, the kit can further include a desiccant to prevent hydrolytic degradation during storage. Useful desiccants for the kits described in this application include without limitation packets enclosing silica gel, clay, activated charcoal, calcium sulfate, calcium chloride and molecular sieves (e.g., zeolites) or the like.

The kit can be employed with bone implants that are configured for minimally invasive midline lumbar fusion, posterior cervical fusion, and oral maxillofacial repair procedures. The kit can also be employed with bone implants used in healing vertebral compression fractures, interbody fusion, additional minimally invasive procedures, posterolateral fusion procedures, correction of adult or pediatric scoliosis, treating long bone defects, osteochondral defects, ridge augmentation (dental/craniomaxillofacial, e.g. edentulous patients), beneath trauma plates, tibial plateau defects, filling bone cysts, wound healing, around trauma, contouring (cosmetic/plastic/reconstructive surgery), and others.

The tray can be made from a metal, thermoform, or a polymer, such as, polyurethane, polyurea, polyether(amide), PEBA, thermoplastic elastomeric olefin, copolyester, and styrenic thermoplastic elastomer, steel, aluminum, stainless steel, titanium, nitinol, metal alloys with high non-ferrous metal content and a low relative proportion of iron, carbon fiber, glass fiber, plastics, ceramics or a combination thereof.

When the tray is made from a thermoform material, the thermoform material may be acrylonitrile butadiene styrene (ABS), polymethyl methacrylate (PMMA, Acrylic, or Plexiglass®), high density polyethylene (HDPE), high impact polystyrene (HIPS), KYDEX™ (PMMA/polyvinyl chloride (PVC) blend), polycarbonate (PC), polyetherimide (PEI or Ultem®), polyethylene terephthalate glycol (PETG), polypropylene (PP), polyvinyl chloride (PVC), thermoplastic polyolefin (TPO).

The tray may also be made from memory shape polymers including, but not limited to, polyethers, polyacrylates, polyamides, poly siloxanes, polyurethanes, polyethers amides, polyurethane/ureas, polyether esters, polynorbornene, cross-linked polymers such as cross-linked polyethylene and cross-linked poly(cyclooctene), inorganic-organic hybrid polymers, and copolymers such as urethane/butadiene copolymers, styrene-butadiene copolymers. Memory shape alloys include, but are not limited to TiNi, CuZnAl, and FeNiAl alloys.

In some embodiments, the tray can include visual indicia, such as, for example, markings that enable a user to measure defined volumes of material being placed into the mesh. In some embodiments, the tray can include length and/or volume markings to assist in filling the mesh.

In various embodiments, the kit may include additional parts along with the bone implant and tray such as spatulas, mixing bowl, wipes, needles, measuring devices, and syringes. The kit may include the mesh in a first compartment. The second compartment may include a vial holding the bone material, diluent and any other instruments needed for the localized implant delivery. A third compartment may include the tray for filling the bone implant. A fourth compartment may include gloves, drapes, wound dressings, and other procedural supplies for maintaining sterility of the implanting process, as well as an instruction booklet, which may include a chart that shows how to implant the bone implant. A fifth compartment may include additional needles, measuring devices, fasteners, and/or sutures. Each tool may be separately packaged in a plastic pouch that is radiation sterilized. A sixth compartment may include an agent for radiographic imaging. A cover of the kit may include illustrations of the implanting procedure and a clear plastic cover may be placed over the compartments to maintain sterility.

Methods of Use

A method of implanting a bone implant at a surgical site beneath the skin of a patient is provided. The method comprises providing a bone implant 10 comprising a covering 18, which covering is configured to be rolled into a diameter D to at least enclose a bone material 12 within the covering; enclosing the bone material in the covering by orientating the covering into a rolled configuration; and placing the bone implant at the surgical site thereby implanting the bone implant at the surgical site. The bone implant implanted by this method can be, for example, bone implant 10 as shown in FIGS. 1-3, 4A, 4B, 5A, 5B, 6, and 7A-7E.

The implantation site corresponds to minimally invasive midline lumbar fusion, posterior cervical fusion, and oral maxillofacial repair procedures. In many aspects, the bone material can be fully demineralized bone fibers and surface demineralized bone chips. The implantation site can also correspond to healing vertebral compression fractures, interbody fusion, additional minimally invasive procedures, posterolateral fusion procedures, correction of adult or pediatric scoliosis, treating long bone defects, osteochondral defects, ridge augmentation (dental/craniomaxillofacial, e.g. edentulous patients), beneath trauma plates, tibial plateau defects, filling bone cysts, wound healing, around trauma, contouring (cosmetic/plastic/reconstructive surgery), and others.

The method can also be employed in a surgical treatment with a patient in a prone or supine position, and/or employ various surgical approaches to the spine, including anterior, posterior, posterior mid-line, direct lateral, and/or anterolateral approaches, and in other body regions. The method may also be employed with procedures for treating the lumbar, cervical, thoracic, sacral, and pelvic regions of a spinal column. The method may also be used on animals, bone models and other non-living substrates, such as, for example, in training, testing and demonstration.

Figure 2:
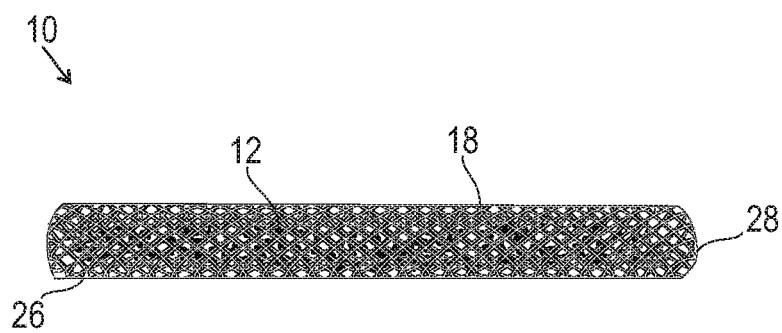
FIG. 2 illustrates a perspective view of a bone implant for enclosing bone material, similar to the bone implant of FIG. 1. The bone material is secured by the rolled mesh, which is sealed at opposite ends and/or along the length of the rolled mesh at the overlap by adhesive.
Figure 3:
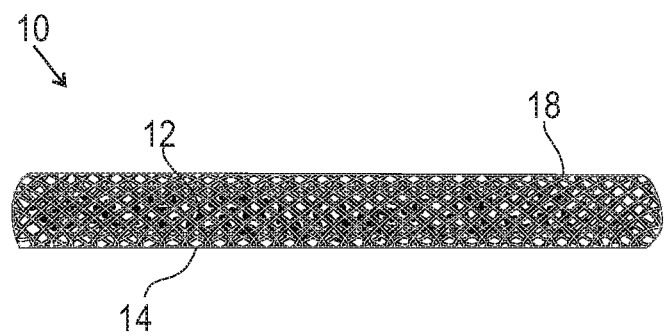
FIG. 3 illustrates a perspective view of a bone implant for enclosing bone material, similar to the bone implant of FIG. 2, where the bone material is secured by the rolled mesh, which is sealed at opposite ends by sutures (not shown).

In some embodiments, the ends of the bone implant can be sealed manually by a user, as shown by FIG. 2, by the user using adhesives 26, 28 or surgical sutures at either ends of the rolled covering. The mesh can alternatively be rolled by the user to enclose or partially enclose the bone material into the bone implant.

In some embodiments, the bone implant may be used in healing vertebral compression fractures, interbody fusion, minimally invasive procedures, posterolateral fusion, correction of adult or pediatric scoliosis, treating long bone defects, osteochondral defects, ridge augmentation (dental/craniomaxillofacial, e.g. edentulous patients), beneath trauma plates, tibial plateau defects, filling bone cysts, wound healing, around trauma, contouring (cosmetic/plastic/reconstructive surgery), and others. The bone implant may be used in a minimally invasive procedure via placement through a small incision, or other means. The size and shape may be designed with restrictions on delivery conditions.

Generally, the bone implant may be applied to a pre-existing defect, to a created channel, or to a modified defect. Thus, for example, a channel may be formed in a bone, or a pre-existing defect may be cut to form a channel, for receipt of the bone implant. The bone implant may be configured to match the channel or defect. In some embodiments, the configuration of bone implant may be chosen to match the channel. In other embodiments, the channel may be created, or the defect expanded or altered, to reflect a configuration of the bone implant. The bone implant may be placed in the defect or channel and, optionally, coupled using attachment mechanisms.

Although the invention has been described with reference to embodiments, persons skilled in the art will recognize that changes may be made in form and detail without departing from the spirit and scope of the invention.

What is claimed is:

1. A bone implant for enclosing a bone material, the bone implant comprising a covering, the covering comprising an interior surface opposing an exterior surface, the interior surface having a first portion enclosing bone material in a first configuration, wherein in the first configuration the covering is rolled to have a first diameter such that the covering can be rolled further to have a second diameter in the second configuration such that the first diameter is greater than the second diameter and the first portion still encloses the bone material in the second configuration, wherein the covering further comprises a first edge, the first edge having a closure member and the closure member comprises a plurality of strands configured to secure the bone material inside the covering after the covering is rolled, and the covering is configured to be adjusted to varying diameters using a sizing ring or cylinder.

2. The bone implant of claim 1, wherein the covering is biodegradable and comprises a mesh.

3. The bone implant of claim 1, wherein the strands are (i) non-resorbable and comprise silk, nylon, cable nylon, polyester, or polypropylene; or (ii) resorbable and biodegradable and comprise polyglycolic acid (PGA), rapid polyglycolic acid (RPGA), polydioxanone (PDO), poliglecaprone or polyglycolide co-caprolactone (PGCL).

4. The bone implant of claim 2, wherein the mesh comprises an interior and an exterior, the interior or exterior of the mesh having a plurality of spaced apart indicia to aid in sizing the covering for implantation.

5. The bone implant of claim 2, wherein the bone material is fully enclosed by the mesh and the mesh is porous to allow influx and efflux of cells.

6. The bone implant of claim 1, wherein the diameter of the rolled covering has a circumference that varies from about 5 mm to about 100 mm and the rolled covering has an adjustable length from about 0.1 cm to about 24 cm.

7. The bone implant of claim 2, wherein the mesh comprises at least one or more of poly(lactide-co-glycolide) (PLGA), polylactide (PLA), polyglycolide (PGA), D-lactide, D,L-lactide, L-lactide, D,L-lactide-co-ε-caprolactone, L-lactide-co-ε-caprolactone, D,L-lactide-co-glycolide-co-ε-caprolactone, poly(D,L-lactide-co-caprolactone), poly(L-lactide-co-caprolactone), poly(D-lactide-co-caprolactone), poly(D,L-lactide), poly(D-lactide), poly(L-lactide), poly(esteramide) or a combination thereof.

8. The bone implant of claim 7, wherein the bone material comprises an osteogenic or chondrogenic protein or peptide or demineralized bone matrix (DBM).

9. The bone implant of claim 1, wherein the covering comprises a biodegradable mesh having shape memory to allow positioning from a planar configuration to a rolled configuration to at least partially enclose the bone material.

10. The bone implant of claim 1, wherein the covering is a tubular configuration and has opposing open edges, the opposing open edges configured to be pulled in opposing directions to reduce the diameter of the covering to at least partially enclose the bone material within the covering.

11. The bone implant of claim 10, wherein the covering is in a tubular conformation having a braided sleeve configuration.

12. The bone implant of claim 1, wherein (i) the covering is loaded with bone material using a funnel having a selected diameter or (ii) the covering is loaded with bone material using a variable diameter funnel.

13. A kit for making a bone implant, the kit comprising a covering, the covering comprising an interior surface opposing an exterior surface, the interior surface having a first portion enclosing bone material in a first configuration, wherein in the first configuration the covering is rolled to have a first diameter such that the covering can be rolled further to have a second diameter in the second configuration such that the first diameter is greater than the second diameter and the first portion still encloses the bone material in the second configuration; and at least one of (i) a plurality of sizing rings or cylinders, the sizing rings or cylinders configured to engage the bone implant to orientate the implant into the first diameter; or (ii) a funnel having a varied diameter, the funnel configured to load the covering with an amount of the bone material, wherein the covering further comprises a first edge, the first edge having a closure member, the closure member comprising a plurality of strands configured to secure the bone material by tying the covering, and the covering is configured to be adjusted to varying diameters using a sizing ring or cylinder.

14. The kit of claim 13, wherein the bone material comprises demineralized bone matrix, allograft, xenograft, ceramic, or a combination thereof.

15. A method of implanting the bone implant of claim 1 at a surgical site, the method comprising providing the bone implant comprising a covering, the covering being configured to be rolled into a diameter to at least partially enclose a bone material within the covering; enclosing the bone material in the covering by orientating the covering into a rolled configuration; and placing the bone implant at the surgical site thereby implanting the bone implant at the surgical site.

16. The method of claim 15, wherein the bone material comprises demineralized bone matrix, allograft, xenograft, ceramic, or a combination thereof.

17. The bone implant of claim 1, wherein the covering has an adjustable diameter such that the covering can adjust from the first diameter to the second diameter without unrolling the covering.

* * * * *